United States Patent [19]
Nielsen et al.

[11] Patent Number: 5,889,002
[45] Date of Patent: Mar. 30, 1999

[54] FUSED 1,2,4-THIADIAZINE AND FUSED 1,4-THIAZINE DERIVATIVES, THEIR PREPARATION AND USE

[75] Inventors: Flemming Elmelund Nielsen, Virum; Holger Claus Hansen, Værløse; John Bondo Hansen, Jyderup; Tina Møller Tagmose, Farum, all of Denmark

[73] Assignee: Novo Nordisk A/S, Bagsvaerd, Denmark

[21] Appl. No.: 785,438

[22] Filed: Jan. 17, 1997

[30] Foreign Application Priority Data

| Jan. 17, 1996 | [DK] | Denmark | 0041/96 |
|---|---|---|---|
| Mar. 5, 1996 | [DK] | Denmark | 0250/96 |
| Mar. 5, 1996 | [DK] | Denmark | 0251/96 |
| Mar. 5, 1996 | [DK] | Denmark | 0252/96 |
| Mar. 5, 1996 | [DK] | Denmark | 0253/96 |
| Mar. 5, 1996 | [DK] | Denmark | 0256/96 |
| Mar. 5, 1996 | [DK] | Denmark | 0259/96 |
| Aug. 27, 1996 | [DK] | Denmark | 0903/96 |

[51] Int. Cl.$^6$ .................. A61K 31/535; A61K 31/54; C07D 498/04; C07D 513/04
[52] U.S. Cl. ................... 514/222.8; 514/224.2; 544/10; 544/48
[58] Field of Search ............. 544/10, 48; 514/224.2, 514/222.8

[56] References Cited

U.S. PATENT DOCUMENTS

| 3,775,312 | 11/1973 | Anderson et al. | 260/243 R |
|---|---|---|---|
| 5,459,138 | 10/1995 | Pirotte et al. | 514/222.8 |

FOREIGN PATENT DOCUMENTS

| 0 618 209 A1 | 10/1994 | European Pat. Off. . |
| 1 368 948 | 10/1974 | United Kingdom . |

OTHER PUBLICATIONS

Berge et al., Journal of Pharmaceutical Sciences, vol. 66, No. 1, pp. 1–19 (Jan. 1977).
Vlahos et al., Metabolism, vol. 40, No. 8, pp. 825–829 (Aug. 1991).
Hamill et al., Pflugers Archiv, vol. 391, pp. 85–100 (1981).
Kotovskaya et al., Plenum Publishing Corporation, vol. 13, No. 4, pp. 54–57 (Apr., 1979).
Bao–Shan Huang et al., "Synthesis And Properties Of The Sulfonyl Analogues Of 4(5)–Aminoimidazole–5(4)–carboxamide, 4(5)–(Formylamino) Imidazole–5(4)–carboxamide, Guanine, and Xanthine", J. Med. Chem., vol. 23, 1980, pp. 575–577.
Bernard Pirotte et al., 3–(Alkylamino)–4H–Pyrido(4,3–e)–1,2,4–thiadiazine 1,1–Dioxides as Powerful Inhibitors Of Insulin Release From Rat Pancreatic B–Cells: A New Class of Potassium Channel Openers, J. Med. Chem., vol. 36, 1993, pp. 3211–3213.
Bernard Pirotte et al., A Pyridothiadiazine (BPDZ 44) As A New And Potent Activator Of ATP–Sensitive K+ Channels, Biochemical Pharmacology, vol. 47, No. 8, 1994, pp. 1381–1386.

William D. Vlahos, "Diabetes Prevention In BB Rats By Inhibition of Endogenous Insulin Secretion", Metabolism, vol. 40, No. 8, 1991, pp. 825–829.
Raffa et al., Farmaco, vol. 29, pp. 411–423 (1974).
Alemzadeh et al., Endocrinology, vol. 133, No. 2, pp. 705–712 (1993).
Hattori et al., The Chemical Society of Japan, vol. 46, No. 6, pp. 1890–1891 (1973).
Stapp, The Journal of Organic Chemistry, vol. 34, No. 4, pp. 1143–1145 (Apr. 1969).
Williams et al., J. Org. Chem., vol. 38, No. 1, pp. 20–26 (1973).
Press et al., Journal of Medicinal Chem., vol. 22, No. 6, pp. 725–731 (1979).
Roma et al., Eur. J. Med., vol. 26, pp. 489–496 (1991).
Barnes et al., J.C.S. Chem. Comm., pp. 776–777 (1973).
Topliss et al., J Org Chem, vol. 28, pp. 2313–2319 (Sep. 1963).
Cronin et al., J Med Chem, vol. 11, pp. 136–139 (1968).
Dillard et al., American Chemical Society, vol. 23, pp. 717–722 (1980).
Huang et al., J Med Chem, vol. 23, pp. 575–577 (1980).
Meyer, Journal of Heterocyclic Chemistry, vol. 6, pp. 407–408 (1969).
Chern et al., J. Heterocyclic Chem., vol. 27, pp. 1909–1915 (Nov.–Dec. 1990).
Stoss et al., Chem. Ber., vol. 109, pp. 2097–2106 (1976).
Taylor et al., Br. J. Pharmacol., vol. 111, pp. 42–48 (1994).
Arkhammar et al., The Journal of Biological Chemistry, vol. 262, No. 12, pp. 5448–5454 (1987).
Bellemin et al., J. Heterocyclic Chem., vol. 21, pp. 1017–1021 (1984).
Tamura et al., Chem. Pharm. Bull., vol. 19, No. 1, pp. 119–123 (1971).
Andersen et al., Chemica Scripta, vol. 29, pp. 45–49 (1989).
Jensen et al., Chemica Scripta, vol. 20, pp. 248–250 (1982).
Kreeze et al., Phosphorus and Sulfur, vol. 29, pp. 41–47 (1986).
Ofitserov et al., Khimiia Geterotsiklicheskikh soedinenii, vol. 8, pp. 1119–1122 (1976).

*Primary Examiner*—Matthew V. Grumbling
*Attorney, Agent, or Firm*—Steve T. Zelson; Valeta Gregg

[57] ABSTRACT

1,2,4-Thiadiazine and 1,4-thiazine derivatives represented by the formula wherein A, B, D, $R^1$, $R^2$, $R^3$ and $R^4$ are defined in the description, compositions thereof and methods for preparing the compounds are described. The compounds are useful in the treatment of diseases of the central nervous system, the cardiovascular system, the pulmonary system, the gastrointestinal system and the endocrinologic system.

31 Claims, No Drawings

FUSED 1,2,4-THIADIAZINE AND FUSED 1,4-THIAZINE DERIVATIVES, THEIR PREPARATION AND USE

CROSS-REFERENCE TO RELATED APPLICATIONS

This application claims priority under 35 U.S.C. 119 of Danish applications 0041/96 filed 17 Jan. 1996, 0250/96 filed 5 Mar. 1996, 0251/96 filed 5 Mar. 1996, 0252/96 filed 5 Mar. 1996, 0253/96 filed 5 Mar. 1996, 0903/96 filed 27 Aug. 1996, 0256/96 filed 5 Mar. 1996, and 0259/96 filed 5 Mar. 1996, the contents of which applications are fully incorporated herein by reference.

FIELD OF THE INVENTION

The present invention relates to fused 1,2,4-thiadiazine and fused 1,4-thiazine derivatives, to methods for their preparation, to compositions comprising the compounds, to the use of these compounds as medicaments and their use in therapy e.g. in the treatment of diseases of the central nervous system, the cardiovascular system, the pulmonary system, the gastrointestinal system and the endocrinological system.

BACKGROUND OF THE INVENTION

Potassium channels play an important role in membrane potential. Among the different types of potassium channels are the ATP-sensitive ($K_{ATP}$-) channels which are regulated by changes in the intracellular concentration of adenosine triphosphate. The $K_{ATP}$-channels have been found in cells from various tissues such as cardiac cells, pancreatic-cells, skeletal muscles, smooth muscles, central neurons and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

Modulators of the $K_{ATP}$-channels have been found to be of importance for the treatment of various diseases. Certain sulphonylureas which have been used for the treatment of non-insulin-dependent diabetes mellitus act by stimulating insulin release through an inhibition of the $K_{ATP}$-channels on pancreatic beta-cells.

The potassium channel openers, which comprise a heterogeneous group of compounds, have been found to be able to relax vascular smooth muscles and have therefore been used for the treatment of hypertension.

In addition, potassium channel openers can be used as bronchodilators in the treatment of asthma and various other diseases.

Furthermore, potassium channel openers have been shown to promote hairgrowth, and have been used for the treatment of baldness.

Potassium channel openers are also able to relax urinary bladder smooth muscle and therefore, can be used for the treatment of urinary incontinence. Potassium channel openers which relax smooth muscle of the uterus can be used for treatment of premature labor.

By acting on potassium channels of the central nervous system these compounds can be used for treatment of various neurological and psychiatric diseases such as Alzheimer, epilepsia and cerebral ischemia.

Recently, it has been shown that Diazoxide (7-chloro-3-methyl-2H-1,2,4-benzothiadiazine 1,1-dioxide) and certain 3-(alkylamino)-4H-pyrido[4,3-e]-1,2,4-thiadiazine 1,1-dioxide derivatives inhibit insulin release by an activation of $K_{ATP}$-channels on pancreatic beta-cells (Pirotte B. et al. Biochem. Pharmacol, 47, 1381–1386 (1994); Pirotte B. et al., J. Med. Chem., 36, 3211–3213 (1993). Diazoxide has furthermore been shown to delay the onset of diabetes in BB-rats (Vlahos W. D. et al. Metabolism 40, 39–46 (1991). In obese zucker rats diazoxide has been shown to decrease insulin secretion and increase insulin receptor binding and consequently improve glucose tolerance and decrease weight gain (Alemzadeh R. et al. Endocrinol. 133, 705–712, 1993). It is expected that such compounds can be used for treatment of diseases characterised by an overproduction of insulin and for the treatment and prevention of diabetes.

EP 618 209 discloses a class of pyridothiadiazine derivatives having an alkyl or an alkylamino group in position 3 of the thiadiazine ring. These compounds are claimed to be agonists at the AMPA-glutamate receptor.

In J. Med. Chem. 1980, 23, 575–577 the synthesis of 4(5)-amino- and formylaminoimidazo-5(4) carboxamide and their properties as agents of chemotherapeutic value are described. Especially, the compounds 3-aminoimidazo[4,5-e]-1,2,4-thiadiazine 1,1-dioxide and N-benzoylaminoimidazo[4,5-e]-1,2,4-thiadiazine 1,1-dioxide are shown.

DESCRIPTION OF THE INVENTION

The present invention relates to fused 1,2,4-thiadiazine and fused 1,4-thiazine derivatives of the general formula I:

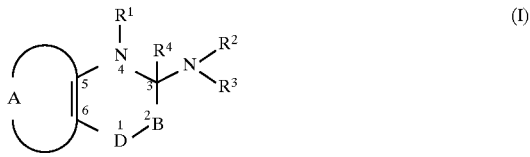

wherein

B represents $>NR^5$ or $>CR^5R^6$, wherein $R^5$ and $R^6$ independently are hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen; or $R^5$ and $R^4$ together represent one of the bonds in a double bond between the atoms 2 and 3 of formula I;

D represents —S(=O)$_2$— or —S(=O)—; or

D—B represents —S(=O)($R^7$)=N— wherein $R^7$ is $C_{1-6}$-alkyl; or aryl or heteroaryl optionally mono- or polysubstituted with halogen, hydroxy, $C_{1-6}$-alkoxy, aryloxy, arylalkoxy, nitro, amino, $C_{1-6}$-monoalkyl- or dialkylamino, cyano, acyl, or $C_{1-6}$-alkoxycarbonyl;

$R^1$ is hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen or $R^4$ together with $R^5$ represent one of the bonds in a double bond between the atoms 2 and 3 of formula I; or $R^1$ together with $R^4$ represent one of the bonds in a double bond between the atoms 3 and 4 of formula I;

$R^2$ is hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen;

$R^3$ is $R^8$; —OR$^8$; —C(=X)R$^8$; —NR$^8$R$^9$; bicycloalkyl, aryl, heteroaryl, arylalkyl or heteroarylalkyl optionally mono- or polysubstituted with halogen, hydroxy, $C_{1-6}$-alkoxy, aryloxy, arylalkoxy, nitro, amino, $C_{1-6}$- monoalkyl- or dialkylamino, cyano, oxo, acyl or $C_{1-6}$-alkoxycarbonyl; or aryl substituted with $C_{1-6}$-alkyl;

wherein $R^8$ is hydrogen; $C_{3-6}$-cycloalkyl or ($C_{3-6}$-cycloalkyl)$C_{1-6}$-alkyl, the $C_{3-6}$-cycloalkyl group optionally being mono- or polysubstituted with $C_{1-6}$-alkyl, halogen, hydroxy or $C_{1-6}$-alkoxy; a 3–6 membered saturated ring system comprising one or more nitrogen-, oxygen- or sulfur atoms; or straight or branched $C_{1-18}$-alkyl optionally mono- or polysubstituted with halogen, hydroxy, $C_{1-6}$-alkoxy, $C_{1-6}$-alkylthio, $C_{3-6}$-cycloalkyl, aryl, aryloxy, arylalkyl, nitro, amino, $C_{1-6}$-monoalkyl- or dialkylamino, cyano, oxo, formyl, acyl, carboxy, $C_{1-6}$-alkoxycarbonyl, or carbamoyl;

X is O or S;

$R^9$ is hydrogen; $C_{1-6}$-alkyl; $C_{2-6}$-alkenyl; $C_{3-6}$-cycloalkyl optionally mono- or polysubstituted with $C_{1-6}$-alkyl, halogen, hydroxy or $C_{1-6}$-alkoxy; or $R^8$ and $R^9$ together with the nitrogen atom form a 3–12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl, nitro, amino, cyano, trifluoromethyl, $C_{1-6}$-monoalkyl- or dialkylamino, oxo; or $R^3$ is

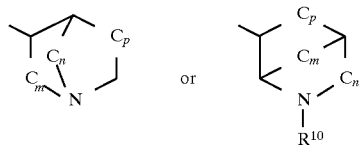

wherein n,m,p independently are 0,1,2,3 and $R^{10}$ is hydrogen; hydroxy; $C_{1-6}$-alkoxy; $C_{3-6}$-cycloalkyl optionally mono- or polysubstituted with $C_{1-6}$-alkyl, halogen, hydroxy or $C_{1-6}$-alkoxy; $C_{1-6}$-alkyl, $C_{2-6}$-alkenyl or $C_{2-6}$-alkynyl optionally mono- or polysubstituted with halogen; or $R^2$ and $R^3$ together with the nitrogen atom forms a 3–12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl, nitro, amino, cyano, trifluoromethyl, $C_{1-6}$-monoalkyl- or dialkylamino or oxo;

A together with carbon atoms 5 and 6 of formula I represents a 5 or 6 membered heterocyclic system comprising one or more nitrogen-, oxygen- or sulfur atoms, the heterocyclic systems optionally being mono- or polysubstituted with halogen; $C_{1-12}$-alkyl; $C_{3-6}$-cycloalkyl; hydroxy; $C_{1-6}$-alkoxy; $C_{1-6}$-alkoxy-$C_{1-6}$-alkyl; nitro; amino; cyano; cyanomethyl; perhalomethyl; $C_{1-6}$-monoalkyl- or dialkylamino; sulfamoyl; $C_{1-6}$-alkylthio; $C_{1-6}$-alkylsulfonyl; $C_{1-6}$-alkylsulfinyl; $C_{1-6}$-alkylcarbonylamino; arylthio, arylsulfinyl, arylsulfonyl, the aryl group optionally being mono- or polysubstituted with $C_{1-6}$-alkyl, halogen, hydroxy or $C_{1-6}$-alkoxy; $C_{1-6}$-alkoxycarbonyl; $C_{1-6}$-alkoxycarbonyl-$C_{1-6}$-alkyl; carbamyl; carbamylmethyl; $C_{1-6}$-monoalkyl- or dialkylaminocarbonyl; $C_{1-6}$-monoalkyl- or dialkylaminothiocarbonyl; ureido; $C_{1-6}$-monoalkyl- or dialkylaminocarbonylamino, thioureido; $C_{1-6}$-monoalkyl- or dialkylaminothiocarbonylamino; $C_{1-6}$-monoalkyl- or dialkylaminosulfonyl; carboxy; carboxy-$C_{1-6}$-alkyl; acyl; aryl, arylalkyl, aryloxy, the aryl group optionally being mono- or polysubstituted with $C_{1-6}$-alkyl, halogen, hydroxy or $C_{1-6}$-alkoxy; (1,2,4-oxadiazol-5-yl)- or (1,2,4-oxadiazol-3-yl)-$C_{1-6}$-alkyl the oxadiazolyl group optionally being substituted with $C_{1-6}$-alkyl or $C_{3-6}$-cycloalkyl; or a 5–6 membered nitrogen containing ring, optionally substituted with phenyl or $C_{1-6}$-alkyl;

provided that A together with carbon atoms 5 and 6 of formula I do not form a pyridine ring and that the following compounds 3-amino-2,5-dihydroimidazo[4,5-e]-1,2,4-thiadiazine 1,1-dioxide and 3-benzylamino-2,5-dihydroimidazo[4,5-e]-1,2,4-thiadiazine 1,1-dioxide are not included;

or a salt thereof with a pharmaceutically acceptable acid or base.

Within its scope the invention includes all optical isomers of compounds of formula I, some of which are optically active, and also their mixtures including racemic mixture thereof.

The scope of the invention also includes all tautomeric forms of the compounds of formula I.

The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{1-6}$-alkylthio" as used herein, alone or in combination, refers to a straight or branched monovalent substituent comprising a lower alkyl group linked through a divalent sulfur atom having its free valence bond from the sulfur atom and having 1 to 6 carbon atoms e.g. methylthio, ethylthio, propylthio, butylthio, pentylthio.

The term "$C_{2-6}$-alkenyl" as used herein refers to an unsaturated hydrocarbon chain having 2–6 carbon atoms and one double bond such as e.g. vinyl, 1-propenyl, allyl, isopropenyl, n-butenyl, n-pentenyl and n-hexenyl.

The term $C_{3-6}$-cycloalkyl" as used herein refers to a radical of a saturated cyclic hydrocarbon with the indicated number of carbons such as cyclopropyl, cyclobutyl, cyclopentyl or cyclohexyl.

The term "$C_{2-6}$-alkynyl" as used herein refers to unsaturated hydrocarbons which contain triple bonds, such as e.g. $-C\equiv CH$, $-C\equiv CCH_3$, $-CH_2C\equiv CH$, $-CH_2CH_2C\equiv CH$, $-CH(CH_3)C\equiv CH$, and the like.

The term "$C_{1-6}$-alkoxy-$C_{1-6}$-alkyl" as used herein refers to a group of 2–12 carbon atoms interrupted by an O such as e.g. $CH_2-O-CH_3$, $CH_2-O-CH_2-CH_3$, $CH_2-O-CH(CH_3)_2$ and the like.

The term "halogen" means fluorine, chlorine, bromine or iodine.

The term "perhalomethyl" means trifluoromethyl, trichloromethyl, tribromomethyl or triiodomethyl.

The terms "$C_{1-6}$-alkyl", "$C_{1-12}$-alkyl" and "$C_{1-18}$-alkyl" as used herein, alone or in combination, refers to a straight or branched, saturated hydrocarbon chain having the indicated number of carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl, 1,2,2-trimethylpropyl and the like. The term "$C_{1-18}$-alkyl" as used herein also includes secondary $C_{3-6}$-alkyl and tertiary $C_{4-6}$-alkyl.

The term "$C_{1-6}$-monoalkylamino" as used herein refers to an amino group wherein one of the hydrogen atoms is substituted with a straight or branched, saturated hydrocarbon chain having the indicated number of carbon atoms such as e.g. methylamino, ethylamino, propylamino, n-butylamino, sec-butylamino, isobutylamino, tert-butylamino, n-pentylamino, 2-methylbutylamino, n-hexylamino, 4-methylpentylamino, neopentylamino, n-hexylamino, 2,2-dimethylpropylamino and the like.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino, and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl, and the like.

The term "$C_{1-6}$-alkoxycarbonyl" as used herein refers to a monovalent substituent comprising a $C_{1-6}$-alkoxy group linked through a carbonyl group; such as e.g. methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like.

The term "3–12 membered mono- or bicyclic system" as used herein refers to a monovalent substituent of formula —$NR^2R^3$ or —$NR^8R^9$ where $R^2$ and $R^3$, or $R^8$ and $R^9$ together with the nitrogen atom form a 3–12 membered mono- or bicyclic system, in which one or more of the carbon atoms may be exchanged with nitrogen, oxygen or sulfur, such as 1-pyrrolidyl, piperidino, morpholino, thiomorpholino, 4-methylpiperazin-1-yl, 7-azabicyclo[2.2.1]heptan-7-yl, tropanyl and the like.

The term "3–6 membered saturated ring system" as used herein refers to a monovalent substituent comprising a monocyclic saturated system containing one or more hetero atoms selected from nitrogen, oxygen and sulfur and having 3–6 members and having its free valence from a carbon atom, e.g. 2-pyrrolidyl, 4-piperidyl, 3-morpholinyl, 1,4-dioxan-2-yl, 5-oxazolidinyl, 4-isoxazolidinyl or 2-thiomorpholinyl.

The term "bicycloalkyl" as used herein refers to a monovalent substituent comprising a bicyclic structure made of 6–12 carbon atoms such as e.g. 2-norbornyl, 7-norbornyl, 2-bicyclo[2.2.2]octyl and 9-bicyclo[3.3.1]nonanyl.

The term "aryl" as used herein refers to phenyl, 1-naphthyl or 2-naphthyl.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine.

The term "arylalkyl" as used herein refers to a straight or branched saturated carbon chain containing from 1 to 6 carbons substituted with an aromatic carbohydride; such as benzyl, phenethyl, 3-phenylpropyl, 1-naphtylmethyl, 2-(1-naphtyl)ethyl and the like.

The term "aryloxy" as used herein refers to phenoxy, 1-naphthyloxy or 2-naphthyloxy.

The term "arylalkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroarylalkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "$C_{1-6}$-alkylsulfonyl" as used herein refers to a monovalent substituent comprising a $C_{1-6}$-alkyl group linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "$C_{1-6}$-monoalkylaminosulfonyl" as used herein refers to a monovalent substituent comprising a $C_{1-6}$-monoalkylamino group linked through a sulfonyl group such as e.g. methylaminosulfonyl, ethylaminosulfonyl, n-propylaminosulfonyl, isopropylaminosulfonyl, n-butylaminosulfonyl, sec-butylaminosulfonyl, isobutylaminosulfonyl, tert-butylaminosulfonyl, n-pentylaminosulfonyl, 2-methylbutylaminosulfonyl, 3-methylbutylaminosulfonyl, n-hexylaminosulfonyl, 4-methylpentylaminosulfonyl, neopentylaminosulfonyl, n-hexylaminosulfonyl and 2,2-dimethylpropylaminosulfonyl.

The term "$C_{1-6}$-dialkylaminosulfonyl" as used herein refers to a monovalent substituent comprising a $C_{1-6}$-dialkylamino group linked through a sulfonyl group such as dimethylaminosulfonyl, N-ethyl-N-methylaminosulfonyl, diethylaminosulfonyl, dipropylaminosulfonyl, N-(n-butyl)-N-methylaminosulfonyl, di(n-pentyl)aminosulfonyl, and the like.

The term "$C_{1-6}$-alkylsulfinyl" as used herein refers to a monovalent substituent comprising a straight or branched $C_{1-6}$-alkyl group linked through a sulfinyl group (—S(=O)—); such as e.g. methylsulfinyl, ethylsulfinyl, isopropylsulfinyl, butylsulfinyl, pentylsulfinyl, and the like.

The term "$C_{1-6}$-alkylcarbonylamino" as used herein refers to an amino group wherein one of the hydrogen atoms is substituted with an acyl group, such as e.g. acetamido, propionamido, isopropylcarbonylamino, and the like.

The term "($C_{3-6}$-cycloalkyl)$C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-alkyl, halogen, hydroxy or $C_{1-6}$-alkoxy; such as e.g. cyclopropylmethyl, (1-methylcyclopropyl)methyl, 1-(cyclopropyl)ethyl, cyclopentylmethyl, cyclohexylmethyl, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chlorophenyl)thio, and the like.

The term "arylsulfinyl" as used herein refers to an aryl group linked through a sulfinyl group (—S(=O)—), the aryl group optionally being mono- or polysubstituted with $C_{1-6}$-alkyl, halogen, hydroxy or $C_{1-6}$-alkoxy; such as e.g. phenylsulfinyl, (4-chlorophenyl)sulfinyl, and the like.

The term "arylsulfonyl" as used herein refers to an aryl group linked through a sulfonyl group, the aryl group optionally being mono- or polysubstituted with $C_{1-6}$-alkyl, halogen, hydroxy or $C_{1-6}$-alkoxy; such as e.g. phenylsulfonyl, tosyl, and the like.

The term "$C_{1-6}$-monoalkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2-2-dimethylpropylaminocarbonyl.

The term "$C_{1-6}$-dialkylaminocarbonyl" as used herein refers to a monovalent substituent comprising a $C_{1-6}$-dialkylamino group linked through a carbonyl group such as dimethylaminocarbonyl, N-ethyl-N-methylaminocarbonyl, diethylaminocarbonyl, dipropylaminocarbonyl, N-(n-butyl)-N-methylaminocarbonyl, di(n-pentyl) aminocarbonyl, and the like.

The term "$C_{1-6}$-monoalkylaminocarbonylamino" as used herein refers to an amino group wherein one of the hydrogen atoms is substituted with a $C_{1-6}$-monoalkylaminocarbonyl group, e.g. methylaminocarbonylamino, ethylaminocarbonylamino, n-propylaminocarbonylamino, isopropylaminocarbonylamino, n-butylaminocarbonylamino, sec-butylaminocarbonylamino, isobutylaminocarbonylamino, tert-butylaminocarbonylamino, and 2-methylbutylaminocarbonylamino.

The term "$C_{1-6}$-dialkylaminocarbonylamino" as used herein refers to an amino group wherein one of the hydrogen atoms is substituted with a $C_{1-6}$-dialkylaminocarbonyl group, such as dimethylaminocarbonylamino, N-ethyl-N-methylaminocarbonylamino, diethylaminocarbonylamino, dipropylaminocarbonylamino, N-(n-butyl)-N-methylaminocarbonylamino, di(n-pentyl) aminocarbonylamino, and the like.

The term "5- or 6-membered heterocyclic system" as used herein refers to: a monocyclic unsaturated or saturated system containing one, two or three hetero atoms selected from nitrogen, oxygen and sulfur and having 5 members, e.g. pyrrole, furan, thiophene, pyrroline, dihydrofuran, dihydrothiophene, imidazole, imidazoline, pyrazole, pyrazoline, oxazole, thiazole, isoxazole, isothiazole, 1,2,3-oxadiazole, furazan, 1,2,3-triazole, 1,2,3-thiadiazole or 2,1,3-thiadiazole; an aromatic monocyclic system containing two or more nitrogen atoms and having 6 members, e.g. pyrazine, pyrimidine, pyridazine, 1,2,4-triazine, 1,2,3-triazine or tetrazine; a non-aromatic monocyclic system containing one or more hetero atoms selected from nitrogen, oxygen and sulfur and having 6 members, e.g. pyran, thiopyran, piperidine, dioxane, oxazine, isoxazine, dithiane, oxathine, thiazine, piperazine, thiadiazine, dithiazine or oxadiazine.

The term "5- or 6-membered nitrogen containing ring" as used herein refers to a monovalent substituent comprising a monocyclic unsaturated or saturated system containing one or more nitrogen atoms and having 5 or 6 members, e.g. pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl, 1,3-dioxolanyl and 1,4-dioxolanyl.

Within its scope the invention includes all optical isomers of compounds of formula I, some of which are optically active, and also their mixtures including racemic mixture thereof.

In a preferred embodiment of the invention the general formula of formula I is selected from

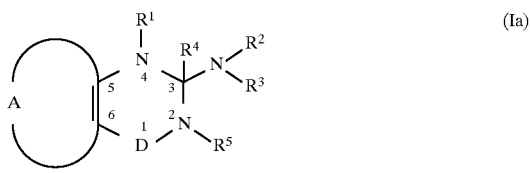

(Ia)

wherein $R^1$ and $R^5$ independently are hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^5$ represent one of the bonds in a double bond between the atoms 2 and 3 of formula I and $R^1$ is as defined above; or $R^4$ together with $R^1$ represent one of the bonds in a double bond between the atoms 3 and 4 of formula I and $R^5$ is as defined above;

D represents —S(=O)$_2$— or —S(=O)—.

In another preferred embodiment of the invention the general formula of formula I is selected from

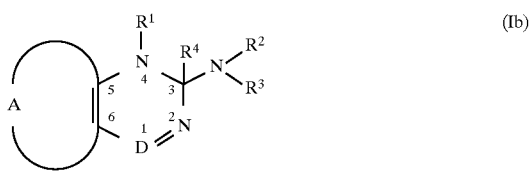

(Ib)

wherein $R^1$ is hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^1$ represent one of the bonds in a double bond between the atoms 3 and 4 of formula I;

D represents —S(=O)$R^7$= wherein $R^7$ is $C_{1-6}$-alkyl; or aryl or heteroaryl optionally mono- or polysubstituted with halogen, hydroxy, $C_{1-6}$-alkoxy, aryloxy, arylalkoxy, nitro, amino, $C_{1-6}$-monoalkyl- or dialkylamino, cyano, acyl or $C_{1-6}$-alkoxycarbonyl.

In another preferred embodiment of the invention the general formula of formula I is selected from

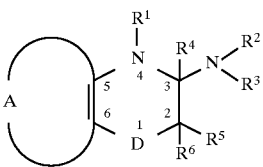

(Ic)

wherein $R^1$, $R^5$ and $R^6$ independently are hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^5$ represent one of the bonds in a double bond between the atoms 2 and 3 of formula I and $R^1$ and $R^6$ are as defined above; or $R^4$ together with $R^1$ represent one of the bonds in a double bond between the atoms 3 and 4 of formula I and $R^5$ and $R^6$ are as defined above;

D represents —S(=O)$_2$— or S(=O).

Preferably, the general formula of formula I is (Ia).

In another preferred embodiment of the invention D is —S(=O)$_2$—.

In another preferred embodiment of the invention $R^1$ is selected from hydrogen, $C_{1-6}$-alkyl, $C_{3-6}$-cycloalkyl or $C_{2-6}$-alkenyl. Preferably $R^1$ is hydrogen or $C_{1-6}$-alkyl.

In another preferred embodiment of the invention $R^1$ together with $R^4$ represent one of the bonds in a double bond between the atoms 3 and 4 of formula I.

In another preferred embodiment of the invention $R^4$ together with $R^5$ represent one of the bonds in a double bond between the atoms 2 and 3 of formula I.

In another preferred embodiment of the invention $R^2$ is selected from hydrogen, hydroxy, $C_{1-6}$-alkyl, $C_{3-6}$-cycloalkyl or $C_{2-6}$-alkenyl. Preferably $R^2$ is hydrogen or $C_{1-6}$-alkyl.

In another preferred embodiment of the invention $R^3$ is selected from $R^8$, —OR$^8$, —NR$^8$R$^9$ or aryl, the aryl group optionally being substituted with $C_{1-6}$-alkyl; wherein $R^8$ is hydrogen; $C_{3-6}$-cycloalkyl; ($C_{3-6}$-cycloalkyl)$C_{1-6}$-alkyl; a 3–6-membered saturated ring system comprising one, two or three nitrogen-, oxygen- or sulfur atoms; or straight or branched $C_{1-18}$-alkyl optionally substituted with halogen, hydroxy, $C_{1-6}$-alkoxy, $C_{1-6}$-alkylthio, $C_{3-6}$-cycloalkyl or aryl; $R^9$ is hydrogen, $C_{1-6}$-alkyl or $C_{3-6}$cycloalkyl; or $R^8$ and $R^9$ together with the nitrogen atom form a 4–6 membered ring, preferably 1-pyrrolidyl, piperdine or morpholino.

In yet another preferred embodiment of the invention $R^3$ is selected from secondary $C_{3-6}$-alkyl, tertiary $C_{4-6}$-alkyl, $C_{3-6}$-cycloalkyl or ($C_{3-6}$-cycloalkyl)methyl optionally mono- or polysubstituted with $C_{1-6}$-alkyl, halogen, hydroxy or $C_{1-6}$-alkoxy. Preferably $R^3$ is selected from isopropyl, 1-methylpropyl, 2-methylpropyl, tert-butyl, 1,1-dimethylpropyl, 1,2-dimethylpropyl, 1,2,2-trimethylpropyl, 2,3-dimethylbutyl, 1-ethylpropyl, 1-ethyl-2-methylpropyl, 1-ethyl-2,2-dimethylpropyl, 2,3,3-trimethylbutyl, 2-methylbutyl, 1,5-dimethylhexyl, 3-methylbutyl, 3-methylhexyl, cyclopropyl, 1-methylcyclopropyl, cyclobutyl, cyclopentyl, cyclohexyl, cyclopropylmethyl, 1-(cyclopropyl)ethyl cyclobutylmethyl, cyclopentylmethyl or cyclohexylmethyl.

In a further preferred embodiment of the invention $R^2$ and $R^3$ together with the nitrogen atom forms a six membered ring, optionally substituted in the 2-position with a $C_{1-6}$-alkyl group, preferably selected from methyl, ethyl or iso-propyl. Preferably the six membered ring is a piperidine, piperazine, morpholine or thiomorpholine ring.

In another preferred embodiment of the invention $R^7$ is selected from $C_{1-6}$-alkyl, phenyl or pyridyl.

In another preferred embodiment of the invention A forms together with carbon atoms 5 and 6 of formula I a 5 membered heterocyclic system containing one hetero atom selected from nitrogen and sulfur, a 5 membered heterocyclic system containing two hetero atoms selected from nitrogen, oxygen and sulfur, a 6 membered aromatic heterocyclic system containing two or three nitrogen atoms, a 6 membered non-aromatic heterocyclic system containing one or two hetero atoms selected from nitrogen, oxygen and sulfur; the heterocyclic systems optionally being mono- or disubstituted with halogen; $C_{1-12}$-alkyl; $C_{3-6}$-cycloalkyl; cyano; cyanomethyl; perhalomethyl; sulfamoyl; $C_{1-6}$-alkylthio; $C_{1-6}$-alkylsulfonyl; $C_{1-6}$-alkylsulfinyl; arylthio, arylsulfinyl, arylsulfonyl, the aryl group optionally being mono- or polysubstituted with $C_{1-6}$-alkyl, halogen, hydroxy or $C_{1-6}$-alkoxy; $C_{1-6}$-alkoxycarbonyl-$C_{1-6}$-alkyl; carbamylmethyl; carboxy-$C_{1-6}$-alkyl; aryloxy; (1,2,4-oxadiazol-5-yl)- or (1,2,4-oxadiazol-3-yl)$C_{1-6}$-alkyl, the oxadiazolyl group optionally being substituted with $C_{1-6}$-alkyl or $C_{3-6}$-cycloalkyl; acyl; or a 5–6 membered nitrogen containing ring, optionally substituted with phenyl or $C_{1-6}$-alkyl.

Preferably, A forms together with carbon atoms 5 and 6 a thieno[3,2-e]- or pyrrolo[3,2-e]-ring, thiophene, imidazole, thiazole, pyrazole, isoxazole or isothiazole, a pyrazino[2,3-e]-, a pyrimido[4,5-e]-, a pyrimido[5,4-e]-, a pyridazino[4,5-e]- or a pyridazino[4,3-e]-ring, thiopyran, piperidine, dioxane, oxazine or dithiane.

Preferred compounds of the invention are:

6-Chloro-3-(1,2-dimethylpropyl)amino-4H-thieno[3,2-e]-1,2,4-thiadiazine 1,1-dioxide;

6-Chloro-3-ethylamino-4H-thieno[3,2-e]-1,2,4-thiadiazine 1,1-dioxide;

6-Chloro-3-isopropylamino-4H-thieno[3,2-e]-1,2,4-thiadiazine 1,1-dioxide;

(S)-6-Chloro-3-(1-phenylethyl)amino-4H-thieno[3,2-e]-1,2,4-thiadiazine 1,1-dioxide;

3-Allylamino-6-chloro-4H-thieno[3,2-e]-1,2,4-thiadiazine 1,1-dioxide;

6-Chloro-3-cyclopropylamino-4H-thieno[3,2-e]-1,2,4-thiadiazine 1,1-dioxide;

6-Chloro-3-hexylamino-4H-thieno[3,2-e]-1,2,4-thiadiazine 1,1-dioxide;

6-Chloro-3-tetradecylamino-4H-thieno[3,2-e]-1,2,4-thiadiazine 1,1-dioxide

6-Chloro-3-methylamino-4H-thieno[3,2-e]-1,2,4-thiadiazine 1,1-dioxide;

3-Benzylamino-6-chloro-4H-thieno[3,2-e]-1,2,4-thiadiazine 1,1-dioxide;

6-Chloro-3-octylamino-4H-thieno[3,2-e]-1,2,4-thiadiazine 1,1-dioxide;

6-Chloro-3-isobutylamino-4H-thieno[3,2-e]-1,2,4-thiadiazine 1,1-dioxide;

6-Chloro-3-(4-phenylbutyl)amino-4H-thieno[3,2-e]-1,2,4-thiadiazine 1,1-dioxide;

6-Chloro-3-(1,5-dimethylhexyl)amino-4H-thieno[3,2-e]-1,2,4-thiadiazine 1,1-dioxide;

6-Chloro-3-propylamino-4H-thieno[3,2-e]-1,2,4-thiadiazine 1,1-dioxide;

(R)-6-Chloro-3-(2-hydroxy-1-methylethyl)amino-4H-thieno[3,2-e]-1,2,4-thiadiazine 1,1-dioxide;

(S)-6-Chloro-3-(2-hydroxy-1-methylethyl)amino-4H-thieno[3,2-e]-1,2,4-thiadiazine 1,1-dioxide;

(R)-3-sec-Butylamino-6chloro-4H-thieno[3,2-e]-1,2,4thiadiazine 1,1-dioxide;

3-Butylamino-6-chloro-4H-thieno[3,2-e]-1,2,4-thiadiazine 1,1-dioxide;

3-Isopropylamino-7-methyl-4,7-dihydro-pyrazolo[4,3-e][1,2,4]thiadiazine 1,1-dioxide;
(S)-6-Chloro-3-(1,2-dimethylpropylamino-4H-thieno[3,2-e]-1,2,4-thiadiazine 1,1-dioxide;
(R)-6-Chloro-3-(1,2-dimethylpropylamino-4H-thieno[3,2-e]-1,2,4-thiadiazine 1,1-dioxide;
3-Isopropylamino-6-methyl-4H-thiazolo[4,5-e]-1,2,4-thiadiazine 1,1-dioxide;
3-Hexylamino-6-methyl-4H-thiazolo[4,5-e]-1,2,4thiadiazine 1,1-dioxide;
6-methyl-3-octylamino-4H-thiazolo[4,5-e]-1,2,4-thiadiazine 1,1-dioxide;
6-Chloro-3isopropylamino-4H-thiazolo[4,5-e]-1,2,4-thiadiazine 1,1-dioxide;
6-Dimethylamino-3-isopropylamino-4H-thiazolo[4,5-e]-1,2,4-thiadiazine 1,1-dioxide;
6-Bromo-3-isopropylamino-4H-thiazolo[4,5-e]-1,2,4-thiadiazine 1,1-dioxide;
3-Isopropylamino-4H-thiazolo[4,5-e]-1,2,4-thiadiazine 1,1-dioxide;
6-Ethylthio-3-isopropylamino-4H-thiazolo[4,5e]-1,2,4-thiadiazine 1,1-dioxide;
3-Isopropylamino-6-methoxy-4H-thiazolo[4,5-e]-1,2,4-thiadiazine 1,1-dioxide;
3-Isopropylamino-4H-thiazolo[5,4-e]-1,2,4-thiadiazine 1,1-dioxide;
6-Bromo-3-isopropylamino-4H-thiazolo[5,4-e]-1,2,4-thiadiazine 1,1-dioxide;
6-Chloro-5-bromo-3-isopropylamino-4H-thieno[3,2-e]-1,2,4-thiadiazine 1,1-dioxide;
5,6-Dibromo-3-isopropylamino-4H-thieno[3,2-e]-1,2,4-thiadiazine 1,1-dioxide;
6-Benzenesulfonyl-3-isopropylamino-4H-thieno[3,2-e]-1,2,4-thiadiazine 1,1-dioxide;
6-Chloro-3-isopropylamino-5-nitro-4H-thieno[3,2-e]-1,2,4-thiadiazine 1,1-dioxide;
3-Isopropylamino-5-methyl-4H-thieno[3,2-e]-1,2,4-thiadiazine 1,1-dioxide;
3-Isopropylamino-5-phenyl-4H-thieno[3,2-e]-1,2,4-thiadiazine 1,1-dioxide;
3-Isopropylamino-6-phenyl-4H-thieno[3,2-e]-1,2,4-thiadiazine 1,1-dioxide;
6-Cyano-3-isopropylamino-5-methyl-4H-thieno[3,2-e]-1,2,4-thiadiazine 1,1-dioxide;
6-Cyano-3-isopropylamino-4H-thieno[3,2-e]-1,2,4-thiadiazine 1,1-dioxide;
3-Isopropylamino-5,6-dimethyl-4H-thieno[3,2-e]-1,2,4-thiadiazine 1,1-dioxide;
5-Cyclopropyl-3-isopropylamino-4H-thieno[3,2-e]-1,2,4-thiadiazine 1,1-dioxide;
3-Isopropylamino-5-(4-methoxyphenyl)-4H-thieno[3,2-e]-1,2,4-thiadiazine 1,1-dioxide;
5-Cyclohexyl-3-isopropylamino-4H-thieno[3,2-e]-1,2,4-thiadiazine 1,1-dioxide;
5-Ethyl-3-isopropylamino-4H-thieno[3,2-e]-1,2,4-thiadiazine 1,1-dioxide;
6-Chloro-3-(3-methylbutyl)amino-4H-thieno[3,2-e]-1,2,4-thiadiazine 1,1-dioxide;
6-Chloro-3-(3-methylhexyl)amino-4H-thieno[3,2-e]-1,2,4-thiadiazine 1,1-dioxide;
3-Isopropylamino-4H-thieno[2,3-e]-1,2,4-thiadiazine 1,1-dioxide;
3-Isopropylamino-7-methyl-4H-thieno[2,3-e]-1,2,4-thiadiazine 1,1-dioxide;
7-Cyano-3-isopropylamino-6-methyl-4H-thieno[2,3-e]-1,2,4-thiadiazine 1,1-dioxide;
3-Isopropylamino-7-ethyl-4H-thieno[2,3-e]-1,2,4-thiadiazine 1,1-dioxide;
7-Cyano-3-isopropylamino-6-methylthio-4H-thieno[2,3-e]-1,2,4-thiadiazine 1,1-dioxide;
7-Cyano-3-isopropylamino-4H-thieno[2,3-e]-1,2,4-thiadiazine 1,1-dioxide;
3-Isopropylamino-4H-thieno[3,4-e]-1,2,4-thiadiazine 1,1-dioxide;
5,7-Dichloro-3-isopropylamino-4H-thieno[3,4-e]-1,2,4-thiadiazine 1,1-dioxide;
3-Cyclopropylamino-7-methyl-4,7-dihydro-pyrazolo[4,3-e][1,2,4]thiadiazine 1,1-dioxide;
3-Hexylamino-7-methyl-4,7-dihydro-pyrazolo[4,3-e][1,2,4]thiadiazine 1,1-dioxide;
7-Methyl-3-octylamino-4,7-dihydro-pyrazolo[4,3-e][1,2,4]thiadiazine 1,1-dioxide;
2,5-Dihydro-3-isopropylamino-imidazo[4,5-e]-1,2,4-thiadiazine 1,1-dioxide;
2,5-Dihydro-3-isopropylamino-5-methyl-imidazo[4,5-e]-1,2,4-thiadiazine 1,1-dioxide;
2,7-Dihydro-3-isopropylamino-7-methyl-imidazo[4,5-e]-1,2,4-thiadiazine 1,1-dioxide;
3-Isopropylamino-4H-pyrazino[2,3-e]-1,2,4-thiadiazine 1,1-dioxide;
3-isopropylamino-5,7-dimethyl-6,8-dioxo-5,6,7,8-tetrahydro-4H-pyrimido[4,5-e]-1,2,4-thiadiazine 1,1-dioxide;
3-(1,2-Dimethylpropyl)amino-2H-pyrazino[2,3-e]-1,2,4thiadiazine 1,1-dioxide;
3-(1-Methylpropyl)amino-2H-pyrazino[2,3-e]-1,2,4-thiadiazine 1,1-dioxide;
3-(2-Methylpropyl)amino-2H-pyrazino[2,3-e]-1,2,4-thiadiazine 1,1-dioxide;
3-Butylamino-2H-pyrazino[2,3-e]-1,2,4-thiadiazine 1,1-dioxide;
3-Propylamino-2H-pyrazino[2,3-e]-1,2,4-thiadiazine 1,1-dioxide;
3-(1,2,2-Trimethylpropyl)amino-2H-pyrazino[2,3-e]-1,2,4-thiadiazine 1,1-dioxide;
6-Chloro-3-(1,2-dimethylpropyl)amino-2H-thieno[3,2-e]-1,2,4-thiadiazine 1,1 dioxide;
6-Chloro-3-(1-methylpropyl)amino-2H-thieno[3,2-e]-1,2,4-thiadiazine 1,1 dioxide;
6-Chloro-3-(2-methylpropyl)amino-2H-thieno[3,2-e]-1,2,4-thiadiazine 1,1 dioxide;
3-Butylamino-6-chloro-2H-thieno[3,2-e]-1,2,4-thiadiazine 1,1 dioxide;
6-Chloro-3-propylamino-2H-thieno[3,2-e]-1,2,4-thiadiazine 1,1 dioxide;
6-Chloro-3-(1,2,2-trimethylpropyl)amino-2H-thieno[3,2-e]-1,2,4-thiadiazine 1,1 dioxide;
3-(1,2-Dimethylpropyl)amino-2H-thieno[2,3-e]-1,2,4-thiadiazine 1,1 dioxide;
3-(1-Methylpropyl)amino-2H-thieno[2,3-e]-1,2,4-thiadiazine 1,1 dioxide;
3-(2-Methylpropyl)amino-2H-thieno[2,3-e]-1,2,4-thiadiazine 1,1 dioxide;
3-Butylamino-2H-thieno[2,3-e]-1,2,4-thiadiazine 1,1 dioxide;
3-Propylamino-2H-thieno[2,3-e]-1,2,4-thiadiazine 1,1 dioxide;
3-(1,2,2-Trimethylpropyl)amino-2H-thieno[2,3-e]-1,2,4-thiadiazine 1,1 dioxide;
3-(1,2-Dimethylpropyl)amino-2H-pyrimido[4,5-e]-1,2,4-thiadiazine 1,1-dioxide;
3-(1-Methylpropyl)amino-2H-pyrimido[4,5-e]-1,2,4-thiadiazine 1,1-dioxide;
3-(2-Methylpropyl)amino-2H-pyrimido[4,5-e]-1,2,4-thiadiazine 1,1-dioxide;

3-Butylamino-2H-pyrimido[4,5-e]-1,2,4-thiadiazine 1,1-dioxide;

3-Propylamino-2H-pyrimido[4,5-e]-1,2,4-thiadiazine 1,1-dioxide;

3-(1,2,2-Trimethylpropyl)amino-2H-pyrimido[4,5-e]-1,2,4-thiadiazine 1,1-dioxide;

3-(1,2-Dimethylpropyl)amino-2H-pyridazino[4,5-e]-1,2,4-thiadiazine 1,1-dioxide;

3-(1-Methylpropyl)amino-2H-pyridazino[4,5-e]-1,2,4-thiadiazine 1,1-dioxide;

3-(2-Methylpropyl)amino-2H-pyridazino[4,5-e]-1,2,4-thiadiazine 1,1-dioxide;

3-Butylamino-2H-pyridazino[4,5-e]-1,2,4-thiadiazine 1,1-dioxide;

3-Propylamino-2H-pyridazino[4,5-e]-1,2,4-thiadiazine 1,1-dioxide;

3-(1,2,2-Trimethylpropyl)amino-2H-pyridazino[4,5-e]-1,2,4-thiadiazine 1,1-dioxide.

The compounds of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases; the pulmonary system; the gastrointestinal system; the central nervous system and the endocrinological system.

Since some $K_{ATP}$-openers are able to antagonize vasospasms in basilar or cerebral arteries the compounds of the present invention can be used for the treatment of vasospastic disorders such as subarachnoid hemorrhage and migraine.

Potassium channel openers hyperpolarize neurons and inhibit neurotransmitter release and it is expected that the present compounds can be used for the treatment of various diseases of the central nervous system, e.g. epilepsia, ischemia and neurodegenerative diseases, and for the management of pain.

By acting on potassium channels of the central nervous system the compounds of the present invention can be used for treatment of various neurological and psychiatric diseases such as Alzheimer, epilepsia and cerebral ischemia.

The compounds of the present invention may also be used for the treatment of diseases associated with decreased skeletal muscle blood flow such as Reynauds disease and intermittent claudication.

Further, the compounds of the invention may be used for the treatment of chronic airway diseases, including asthma, and for treatment of detrusor muscle instability secondary to bladder outflow obstruction and therefore for kidney stones by aiding their passage along the ureter. Potassium channel openers also relax urinary bladder smooth muscle, thus, the compounds of the present invention can be used for the treatment of urinary incontinence.

The present compounds could also be used for treatment of conditions associated with disturbances in gastrointestinal mobility such as irritable bowel syndrome. Additionally these compounds can be used for the treatment of premature labor and dysmenorrhea.

Further, potassium channel openers promote hairgrowth, therefore, the compounds of the present invention can be used for the treatment of baldness.

In diseases such as nesidioblastosis and insulinoma in which a hypersecretion of insulin causes severe hypoglycemia the compounds of the present invention can be used to reduce insulin secretion. In obesity hyperinsulinemia and insulin resistance is very frequently encountered. This condition could lead to the development of noninsulin dependent diabetes (NIDDM). It is expected that potassium channel openers and hence the compounds of the present invention can be used for counteracting the hyperinsulinemia and thereby prevent diabetes and reduce obesity. In overt NIDDM treatment of hyperinsulinemia with potassium channel openers, and hence the present compounds, can be of benefit in restoring glucose sensitivity and normal insulin secretions.

In early cases of insulin dependent diabetes (IDDM) or in prediabetic cases, potassium channel openers and hence the present compounds can be used to induce betacell rest which may prevent the progression of the autoimmune disease.

Compounds of the present invention which act as blockers of $K_{ATP}$-channels can be used for the treatment of NIDDM.

Preferably, the compounds of the present invention may be used for treatment or prevention of diseases of the endocrinological system such as hyperinsulinemia and diabetes.

Accordingly, in another aspect the invention relates to a compound of the general formula I or a pharmaceutically acceptable acid addition salt thereof for use as a therapeutically acceptable substance, preferably for use as a therapeutically acceptable substance in the treatment of hyperinsulinemia and treatment or prevention of diabetes.

Furthermore, the invention also relates to the use of the inventive compounds of formula I as medicaments useful for treating hyperinsulinemia and treating or preventing diabetes.

In yet another aspect, the present invention relates to methods of preparing the above mentioned compounds. The method comprises:

a) reacting a compound of formula II:

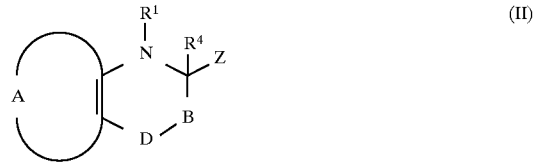

wherein A, B, D, $R^1$ and $R^4$ are as defined above and Z is a leaving group such as alkoxy, alkylthio, halogen, preferentially chloro, bromo, iodo, trimethylamino, or methylsulfonyl with a compound of formula III:

wherein $R^2$ and $R^3$ are defined above to form a compound of the general formula I using procedures described by e.g. T. H. Cronon et al., *J. Med. Chem.* 11, 136 (1968); L. Raffa et al., *Farmaco Ed. Sci.* 29, 411 (1974); B. Pirotte et al., *J. Med. Chem.* 36, 3211 (1993).

Another method comprises:

b) reacting a compound of formula IV:

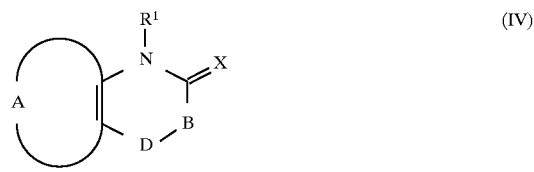

wherein $R^1$ is hydrogen and A, B, D and X are as defined above, or B is NH and $R^1$, A, D and X are as defined above, with the compound of formula III, or a suitable salt thereof in the presence of $P_2O_5$ and a high boiling tertiary amine or a suitable salt therof using a procedure described by Jensen K. G. and Pedersen E. B., *Chem. Scr.,* 20, 248–250 (1988) and Andersen L., Nielsen F. E. and Pedersen E. B., *Chem. Scr.,* 29, 45–49 (1989), to form a compound of the general formula I.

c) reacting a compound of the formula IV:

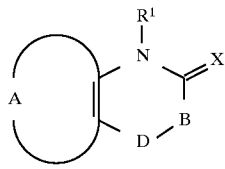
(IV)

wherein $R^1$ is hydrogen and A, B, D and X are as defined above or B is NH and $R^1$, A, D and X are as defined above, with a compound of the formula III, or a suitable salt thereof in the presence of titanium tetrachloride and a solvent with which it may form a complex, like e.g. tetrahydrofuran, or a mixture of toluene and anisole, according to the methods described in R. I. Fryer, J. V. Earley, G. F. Field, W. Zally, and L. H. Stembach, *J. Org. Chem.* 34, 1143–1145 (1969); J. B. Press et al., *J. Med. Chem.* 22 725–731 (1979); or G. Roma et al. *Eur. J. Med. Chem.* 26, 489–496 (1991), to form a compound of the general formula I.

d) reacting a compound of formula V

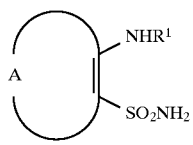
(V)

wherein $R^1$ and A are as defined above, with a compound of formula VI

R³NCO (VI)

wherein $R^3$ is as defined above using the method described by Chern J. W. et al., *J. Heterocycl. Chem.,* 27, 1909–1915 (1990), to form a compound of the general formula I wherein D is $SO_2$, B is >$NR^5$, $R^2$ is H, and $R^4$ and $R^5$ together form a bond.

e) reacting a compound of the formula V

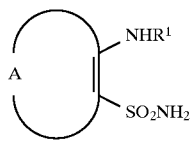
(V)

wherein $R^1$ and A are as defined above, with a compound of formula VII

R³NHC(=O)Cl (VII)

wherein $R^3$ is as defined above using the method described by Chern J. W. et al., *J. Heterocycl. Chem.,* 27, 1909–1915 (1990), to form a compound of the general formula I wherein D is $SO_2$, B is >$NR^5$, $R^2$ is H, and $R^4$ and $R^5$ together form a bond.

f) reacting a compound of the formula V

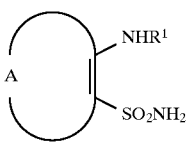
(V)

wherein $R^1$ and A are defined as above, with a compound of formula VIII

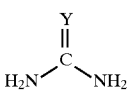
(VIII)

wherein Y is NH or S, or a suitable salt thereof using procedures described by Kotovskaya S. K. et al., *Khim.-Farm. Zh.,* 13, 54–57 (russ.) (1979) and Topliss J. G. et al., *J. Org. Chem.,* 28, 2313 (1963), to form a compound of the general formula I, wherein D is $SO_2$, B is >$NR^5$, $R^4$ and $R^5$ together form a bond, and $R^2$ and $R^3$ are H.

g) reacting in the presence of a base a compound of formula IX

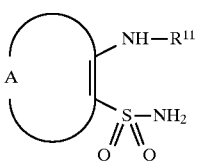
(IX)

or a suitable salt thereof, wherein $R^{11}$ is $R^1$ or EtOC(=O), wherein $R^1$ and A are defined as above, with a compound of formula X

R³N=C=S (X)

wherein $R^3$ is as defined above, to form an adduct which may have either of the two structures XI or XII or be a mixture of the two

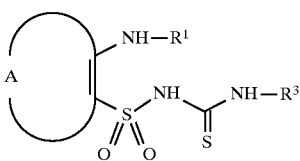
(XI)

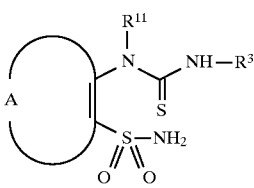
(XII)

either of which by ring-closure, e.g. by treatment with phosgene in a suitable solvent, forms a compound of the general formula I, if $R^{11}$ is $R^1$, wherein D is S(=O)$_2$, B is >$NR^5$, $R^2$ is H, and $R^4$ and $R^5$ together is a bond, and a compound of the general formula XIII if $R^{11}$ is EtOC(=O);

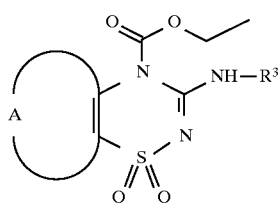

(XIII)

h) hydrolyzing and subsequently decarboxylating a compound of the general formula XIII

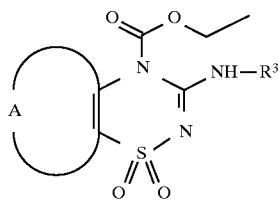

(XIII)

to form a compound of the general structure I, wherein D is S(=O)$_2$, B is >NR$^5$, R$^1$ and R$^2$ are H, and R$^4$ and R$^5$ together form a bond, e.g. by heating the starting compound in aqueous base.

The starting materials are either known compounds or compounds which may be prepared in analogy with the preparation of known compounds or in analogy with known methods as described by e.g Huang B.-S., et al., *J. Med. Chem.*, 23, 575–7 (1980), Ofitserov V. I. et al., *Khim. Geterotsikl. Soedin.*, 1119–22 (russ.) (1976), Topliss J. G., U.S. Pat. No. 3,641,017 (1972), Kotovskaya S. K. et al., *Khim.-Farm. Zh.*, 13, 54–57 (russ.) (1979), Meyer R. F., *J. HeterocycL. Chem.*, 6, 407–408 (1969) and Hattori M., Yoneda M., and Goto M., *Bull. Chem. Soc. Jap.*, 46,1890–1 (1973), Williams T. R. and Cram D. J., *J. Org. Chem.*, 38, 20–26 (1973), Barnes A. C., Kennewell P. D. and Taylor J. B., *J. Chem. Soc. Chem. Commun.*, 1973, 776–777, Stoss and Satzinger, *Chem. Ber.*, 109, 2097 (1976), Kresze G., Hatjiissaak A., *Phosphorus Sulfur*, 29, 41–47 (1987), Dillard R. D., Yen T. T., Stark P., Pavey D. E., *J. Med. Chem.*, 23, 717–722 (1980).

PHARMACOLOGICAL METHODS

The ability of the compounds to interact with potassium channels can be determined by various methods. When patch-clamp techniques (Hamill O. P., Marty A., Nefer E., Sakman B. and Sigworth F. J., *Plügers Arch.*, 391, 85–100 (1981)) are used the ionic current through a single channel of a cell can be recorded.

The activity of the compounds as potassium channel openers can also be measured as relaxation of rat aortas rings according to the following procedure:

A section of rat thoracic aorta between the aortic arch and the diaphragm was dissected out and mounted as ring preparations as described by Taylor P. D. et al, *Brit J. Pharmacol*, 111, 42–48 (1994).

After a 45 min. equilibration period under a tension of 2 g, the preparations were contracted to achieve 80% of the maximum response using the required concentration of phenylephrine. When the phenylephrine response reached a plateau, potential vasodilatory agents were added cumulatively to the bath in small volumes using half log molar increments at 2 min intervals. Relaxation was expressed at the percentage of the contracted tension. The potency of a compound was expressed as the concentration required to evoke a 50% relaxation of the tissue.

Relaxation of rat aorta rings

| Compound | EC50 micro M |
| --- | --- |
| 1 | 1.2 |
| 2 | 15 |
| 16 | 6.1 |

In the pancreatic b-cell the opening of the $K_{ATP}$-channels can be determined by measuring the subsequent change in the concentration of cytoplasmic free Ca$^{2+}$ concentration according to the method of Arkhammer P. et al., *J. Biol. Chem.*, 262, 5448–5454 (1987).

$^{86}$Rb$^+$ efflux from a β-cell line

The RIN 5F cell line was grown in RPMI 1640 with Glutamax I, supplemented with 10% fetal calf serum (from GibcoBRL, Scotland, UK) and maintained in an atmosphere of 5% CO$_2$/95% air at 37° C. The cells were detached with a Trypsin-EDTA solution (from GibcoBRL, Scotland, UK), resuspended in medium, added 1 mCi/ml $^{86}$Rb$^+$ and replated into microtiter plates (96 well cluster 3596, sterile, from Costar Corporation, Massachusetts, U.S.A.) at a density of 50000 cells/well in 100 ml/well, and grown 24 hours before use in assay.

The plates were washed 4 times with Ringer buffer (150 mM NaCl, 10 mM Hepes, 3.0 mM KCl, 1.0 mM CaCl$_2$, 20 mM Sucrose, pH 7.1). Eighty μl Ringer buffer and 1 μl control- or test compound dissolved in DMSO was added. After incubation 1 h at room temperature with a lid, 50 μl of the supernatant was transferred to PicoPlates (Packard Instrument Company, Connecticut, U.S.A.) and 100 μl MicroScint40 (Packard Instrument Company, Connecticut, U.S.A.) added. The plates were counted in TopCount (Packard Instrument Company, Connecticut, U.S.A.) for 1 min/well at the $^{32}$P program.

The calculation of EC$_{50}$ and E$_{max}$ was done by SlideWrite (Advanced Graphics Software, Inc., California, U.S.A.) using a four parameter logistic curve: $y=(a-d)/(1+(x/c)^b)+d$, where a=the activity estimated at concentration zero, b=a slope factor, c=the concentration at the middle of the curve and, d=the activity estimated at infinite concentration. EC$_{50}$=c and E$_{max}$=d, when the curve is turned of at infinite concentrations.

Inhibition of Rb-efflux in rin 5F cells

| Compound | EC50 micro M |
| --- | --- |
| 1 | 2.7 |
| 16 | 5.9 |

The compounds according to the invention are effective over a wide dosage range. In general satisfactory results are obtained with dosages from about 0.05 to about 1000 mg, preferably from about 0.1 to about 500 mg, per day. A most preferable dosage is about 5 mg to about 200 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of an ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet, appropriate for use in this method, may be prepared by conventional tabletting techniques and contains:

| | |
|---|---|
| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

Due to their high degree of activity, the compounds of the invention may be administered to an animal in need of such treatment, prevention, elimination, alleviation or amelioration of various diseases as mentioned above and especially of diseases of the endocrinological system such as hyperinsulinemia and diabetes. Such animals include both domestic animals, e.g. household pets, and non-domestic animals such as wildlife. Preferably the animal is a mammal especially a human.

EXAMPLES

The process for preparing compounds of formula I and preparations containing them is further illustrated in the following examples which, however, are not to be construed as limiting.

Example 1

6-Chloro-3-(1,2-dimethylpropyl)amino-4H-thieno[3,2-e]-1,2,4-thiadiazine 1,1-dioxide

A a) Ethyl 5-chloro-2-sulfamoylthiophene-3-carboxylate

A solution of 2-(N-tert-butylsulfamoyl)-5-chlorothiophene-3-carboxylic acid (60.0 g; 0.201 mol) made by the procedure described by B. Unterhalt and S. Moghaddam, Pharmazie 49, 115–117 (1994) in 700 ml of abs. ethanol saturated with hydrogen chloride was heated with stirring at reflux for 17 h. The cooled solution was evaporated to dryness and the residue was purified by trituration with water and dried to give 52.3 g (96%) of the title compound; $^1$H-NMR (DMSO-d$_6$): δ 1.31 (t, J=7 Hz, 3H, CH$_3$), 4.32 (q, J=7 Hz, 2H, CH$_2$), 7.55 (s, 1H), 7.77 (br. s, 2H, NH$_2$).

b) 5-Chloro-2-sulfamoylthiophene-3-carbohydrazide

Ethyl 5-chloro-2-sulfamoylthiophene-3-carboxylate (50.0 g; 0.185 mol) was added in one portion to 98% hydrazine hydrate (50 ml) with stirring at ambient temperature. The reaction was slightly exothermic. The solution was stirred for 90 min. and concentrated. The residue was crystallised by trituration with 250 ml of water and the mixture was adjusted to pH 2–3 with conc. hydrochloric acid and stirred for 30 min. at 0° C. The product was isolated by filtration, washed with water and dried to give 42.2 g (89%) of the title compound; $^1$H-NMR (DMSO-d$_6$): δ 4.7 (br. s, 2H, NH$_2$), 7.49 (s, 1H), 7.71 (br. s, 2H, NH$_2$), 9.94 (br. s, 1H, NH).

c) 5-Chloro-2-sulfamoyl-3-thenoyl azide

A solution of sodium nitrite (3.0 g; 43.4 mmol) in 20 ml of water was added dropwise with stirring at 0° C. to a solution of 5-chloro-2-sulfamoylthiophene-3-carbohydrazide (10.0 g; 39.1 mmol) in 80 ml of 1M hydrochloric acid and the mixture was stirred for 15 min. The precipitate was isolated by filtration, washed with water and dried to give 9.93 g (96%) of the title compound; $^1$H-NMR (DMSO-d$_6$): δ 7.55 (s, 1H), 7.97 (br. s, 2H, NH$_2$).

d) 6-Chloro-2,3-dihydro-3-oxo-4H-thieno[3,2-e]-1,2,4-thiadiazine 1,1-dioxide

5-Chloro-2-sulfamoyl-3-thenoyl azide (7.0 g; 26.2 mmol) was added in portions to 50 ml of refluxing dry toluene during 10 min. The mixture was stirred for 5 min. and cooled on an ice bath. The precipitate was isolated by filtration, washed with toluene and dried to give 5.90 g (94%) of the title compound; m.p. 245°–248° C. decomp.; $^1$H-NMR (DMSO-d$_6$): δ 6.93 (s, 1H), 11.98 (s, 1H, NH).

e) 6-Chloro-3-(1,2-dimethylpropyl)amino-4H-thieno[3,2-e]-1,2,4-thiadiazine 1,1-dioxide Phosphorus pentoxide (2.84 g; 20 mmol), N,N-dimethylcyclohexylamine (5 ml, 33 mmol) and 1,2-dimethylpropylamine hydrochloride (2.47 g; 20 mmol) were carefully mixed in a three necked flask equipped with mechanical stirring and condenser with drying tube. The mixture was heated on an oil bath at 200° C. until a homogeneous mass was obtained. Then 6-chloro-2,3-dihydro-3-oxo-4H-thieno[3,2-e]-1,2,4-thiadiazine 1,1-dioxide (1.2 g; 5 mmol) was added and the mixture was stirred at 240° C. for 45 min. The mixture was allowed to cool to about 100° C., 150 ml of water was added and stirring was continued at ambient temperature for approximately 1 h. The hydrolysed mixture was filtered and the dark precipitate was washed with water and dissolved in boiling ethanol, treated with charcoal, filtered and finally evaporated to dryness. Flash chromatography (ethyl acetate/silica gel) afforded 105 mg (7%) of the pure title compound; m.p. 216°–218° C.; $^1$H-NMR (DMSO-d$_6$): δ 0.90 (d, 6H, CH(CH$_3$)$_2$), 1.08 (d, 3H, NCHCH$_3$), 1.75 (m, 1H, CH(CH$_3$)$_2$), 3.65 (m, 1H, NHCH), 7.11 (br. s, 2H, 5-H+NH), 10.68 (s, 1H, NH); MS m/e: 307/309 (M$^+$).

Alternatively, 6-chloro-3-(1,2-dimethylpropyl)amino-4H-thieno[3,2-e]-1,2,4-thiadiazine 1,1-dioxide could be prepared by the following procedure.

B a) 3,6-Dichloro-4H-thieno[3,2-e]-1,2,4-thiadiazine 1,1-dioxide

A suspension of 6-chloro-2,3-dihydro-3-oxo-4H-thieno[3,2-e]-1,2,4-thiadiazine 1,1-dioxide (10.75 g, 0.045 mol) in phosphorus oxychloride (100 ml) was cooled on an ice bath and dry pyridine (7.3 ml, 0.09 mol) was added dropwise at such a rate that the temperature did not exceed 10° C. The mixture was then heated at 95°–100° C. for 16 h, and cooled to room temperature. A yellow precipitate was removed by filtration, and the filtrate was concentrated in vacuo. To the residue was added 200 g of ice, and the resulting mixture was stirred for 1 h, and filtered. The isolated solid was dissolved in saturated aqueous sodium hydrogen carbonate (100 ml), and filtered to remove a small amount of insoluble material. After treatment with decolorising charcoal the filtrate was adjusted to pH 2 with 4M hydrochloric acid and the precipitate that formed was filtered, washed with water and dried to yield 5.55 g (48%) of the title compound; mp >240° C. decomp.

b) 6-Chloro-3-(1,2-dimethylpropyl)amino-4H-thieno[3,2-e]-1,2,4-thiadiazine 1,1-dioxide A solution of 3,6-dichloro-4H-thieno[3,2-e]-1,2,4-thiadiazine 1,1-dioxide (0.5 g, 1.94 mmol) in 1,2-dimethylpropylamine (5 ml) was stirred for 48 h at 100° C in a sealed flask. The cooled mixture was concentrated in vacuo and the residue was stirred with water (20 ml) followed by adjustment to pH 2 with 4M hydrochloric acid. The initially formed gummy product crystallised by stirring the mixture for about 2 h at 0° C. The precipitate was isolated by filtration, washed with water, and recrystallised from ethyl acetate/methanol followed by drying in vacuo at 60° C. over night to give 0.43 g (72%) of the pure title compound.

Example 2

6-Chloro-3-ethylamino-4H-thieno[3,2-e]-1,2,4-thiadiazine 1,1-dioxide

Phosphorus pentoxide (2.84 g, 20 mmol), N,N-dimethylcyclohexylamine (3 ml, 20 mmol) and ethylamine hydrochloride (1.63 g, 20 mmol) were carefully mixed and heated with stirring on an oil bath at 180° C. for 20 min. To the homogeneous mass was added 6-chloro-2,3-dihydro-3-oxo-4H-thieno[3,2-e]-1,2,4-thiadiazine 1,1-dioxide (1.2 g, 5 mmol) and the mixture was stirred at 180° C. for 5 h. After cooling to ca. 100° C., water (150 ml) was added and the mixture was stirred for 1 h at room temperature. Then the mixture was extracted with ethyl acetate (3×100 ml). The organic phase was washed with saturated aqueous sodium hydrogen carbonate, dried and evaporated to dryness. The residue was recrystallised from ethyl acetate/methanol to give 282 mg (21%) of the pure title compound; m.p. 271°–274° C.; $^1$H-NMR (DMSO-d$_6$): δ 1.11 (t, 3H, CH$_3$), 3.22 (m, 2H, CH$_2$), 7.04 (s,1H, 5-H), 7.3 (br. s, 1H, NH), 11.1 (br. s, 1H, NH); MS m/e: 265/267 (M$^+$); (C$_7$H$_8$N$_3$Cl$_1$O$_2$S$_2$) calc. C 31.64 H 3.03 N 15.81, found C 31.57 H 3.12 N 15.63.

Example 3

6-Chloro-3-isopropylamino-4H-thieno[3,2-e]-1,2,4-thiadiazine 1,1-dioxide

A

The title compound was made by a similar procedure as described in example 2 except that isopropylamine hydrochloride (1.91 g, 20 mmol) was used as the primary amine. Yield: 150 mg (11%); m.p. 281°–283° C. (ethyl acetate); $^1$H-NMR (DMSO-d$_6$): δ 1.15 (d, 6H, CH(CH$_3$)$_2$), 3.88 (m, 1H, CH), 7.08 (s, 1H, 5-H), 7.20 (br. d, 1H, NH), 10.74 (br. s, 1H, NH); MS m/e: 279/281 (M$^+$); (C$_8$H$_{10}$N$_3$Cl$_1$O$_2$S$_2$) calc. C 34.35 H 3.60 N 15.02, found C 34.37 H 3.70 N 14.95.

Alternatively, 6-chloro-3-isopropylamino-4H-thieno[3,2-e]1,2,4-thiadiazine 1,1-dioxide could be prepared by the following procedure

B a) 3-Amino-5-chlorothiophene-2-sulfonic acid tert-butylamide

A solution of 38.1 g (0.15 mol) of 5-chlorothiophene-2-sulfonic acid tert-butylamide in 300 ml of dry tetrahydrofuran was cooled to −70° C, and n-BuLi (190 ml, 1.6M in hexane) was added, maintaining the temperature <−65° C. After addition, the mixture was allowed to warm to −20° C. and stirred at this temperature for 30 min. A solution of p-toluenesulfonyl azide (34 g, 0.17 mol) in 100 ml of dry tetrahydrofuran was added, maintaining the temperature at −20° C., and the cooling bath was removed. After the mixture had reached room temperature, water (100 ml) was added. The organic phase was isolated and the aqueous phase was extracted with toluene (2×50 ml). To the combined organic phases was added hexadecyltributylphosphonium bromide (7.62 g, 15 mmol) followed by the dropwise addition of a solution of sodium borohydride (6.58 g, 0.174 mol) in 20 ml of water with stirring and cooling to room temperature. The mixture was stirred over night at room temperature, and water (100 ml) was added. The organic phase was isolated, washed with water (2×100 ml), dried, and evaporated to dryness. The oily residue was dissolved in ethyl acetate (150 ml) and washed with 1N sodium hydroxide (6×100 ml). The organic phase was dried with sodium sulfate, and evaporated to afford a quantitative yield (40.6 g) of crude title compound as an oil, which was used without further purification in the next step.

b) 3-Amino-5-chlorothiophene-2-sulfonamide hydrochloride

3-Amino-5-chlorothiophene-2-sulfonic acid tert-butylamide (40.4 g) was heated with stirring at 50° C. to 60° C. in 200 ml of conc. hydrochloric acid for 2.5 h. The crude product was isolated from the cooled mixture by filtration, dried and purified by trituration with 60 ml of ether to afford 17.8 g (48%) of the title compound. $^1$H-NMR (DMSO-d$_6$): δ 6.64 (s, 1H), 6.84 (very br., 5H).

c) N-(3-Amino-5-chloro-2-thienylsulfonyl)-N'-isopropylthiourea

Potassium tert-butoxide (0.49 g, 4.4 mmol) was added to a solution of 3-amino-5-chlorothiophene-2-sulfonamide hydrochloride (0.5 g, 2.0 mmol) in dry N,N-dimethylformamide (5 ml) with stirring on an ice bath. After 5 min, isopropyl isothiocyanate (0.26 ml, 2.4 mmol) was added dropwise to the resulting suspension, and the mixture was stirred for 30 min at 0° C. The cooling bath was removed, and stirring was continued at room temperature for 30 min. The solvent was evaporated at <50° C., and the residue was taken up in 25 ml of water, treated with decolorising charcoal, and filtered. Acidification of the filtrate with acetic acid to pH 3–4 and filtration afforded 0.50 g (80%) the title compound; mp 142.0°–142.5° C. decomp., $^1$H-NMR (DMSO-d$_6$): δ 1.12 (d, 6H), 4.25 (m, 1H), 6.48 (br s, 2H), 6.65 (s, 1H), 8.02 (d, 1H), 11.2 (br s, 1H).

d) 6-Chloro-3-isopropylamino-4H-thieno[3,2-e]1,2,4-thiadiazine 1,1-dioxide

Phosgene (1.14 ml, 20% in toluene) was added dropwise to a solution of N-(3-amino-5-chloro-2-thienylsulfonyl)-N'-isopropylthiourea (0.63 g, 2.0 mmol) and dry triethylamine (0.56 ml, 4.0 mmol) in dry tetrahydrofuran (10 ml) with stirring at 0° C. The mixture was stirred for 1 h at 0° C., and evaporated to dryness. The residue was triturated with water, and the precipitate was isolated by filtration, washed with water and dried affording 0.52 g (93%) of the title compound.

Alternatively 6-chloro-3-isopropylamino-4H-thieno[3,2-e]-1,2,4-thiadiazine 1,1-dioxide could be prepared by the following procedure.

C

A solution of 3,6-dichloro-4H-thieno[3,2-e]-1,2,4-thiadiazine 1,1-dioxide (1.5 g, 5.83 mmol) in isopropylamine (10 ml) was stirred in a Teflon-lined stainless steel pressure bomb at 100° C. for 24 h. Excess amine was evaporated, and the residue was stirred in water (25 ml) followed by the addition of 4M hydrochloric acid to pH 2. The mixture was stirred on an ice bath for about 1 h to afford 0.99 g (61%) of the title compound as a crystalline product.

Example 4

(S)-6-Chloro-3-(1-phenylethyl)amino-4H-thieno[3,2-e]-1,2,4-thiadiazine 1,1-dioxide The title compound was prepared from 3-amino-5-chlorothiophene-2-sulfonamide hydrochloride and L-α-methylbenzyl isothiocyanate by a procedure analogous to the procedure described in example 3Bc–d; mp 195°–204° C. (ethyl acetate), $^1$H-NMR (DMSO-d$_6$): δ 1.46 (d, 3H), 4.95 (m, 1H), 7.1 (s, 1H), 7.2–7.45 (m, 5H), 7.78 (br. s, 1H), 10.85 (s, 1H).

Example 5

3-Allylamino-6-chloro-4H-thieno[3,2-e]-1,2,4-thiadiazine 1,1-dioxide

The title compound was prepared from 3-amino-5-chlorothiophene-2-sulfonamide hydrochloride and allyl isothiocyanate by a procedure analogous to the procedure described in example 3Bc–d; mp 217°–221° C.; $^1$H-NMR (DMSO-d$_6$): δ 3.83 (distorted t, 2H), 5.08–5.27 (m, 2H), 5.75–5.99 (m, 1H), 7.07 (s, 1H), 7.49 (br. t, 1H), 11.1 (s, 1H).

Example 6

6-Chloro-3-cyclopropylamino-4H-thieno[3,2-e]-1,2,4-thiadiazine 1,1-dioxide

The title compound was prepared from 3-amino-5-chlorothiophene-2-sulfonamide hydrochloride and cyclopropyl isothiocyanate by a procedure analogous to the procedure described in example 3Bc–d; mp 272°–273° C.; $^1$H-NMR (DMSO-d$_6$): δ 0.55 (m, 2H), 0.78 (m, 2H), 2.6 (m, 1H), 7.10 (s, 1H), 7.88 (br. s, 1H), 10.95 (br. s, 1H).

Example 7

6-Chloro-3-hexylamino-4H-thieno[3,2-e]-1,2,4-thiadiazine 1,1-dioxide

The title compound was prepared from 3-amino-5-chlorothiophene-2-sulfonamide hydrochloride and n-hexyl isothiocyanate by a procedure analogous to the procedure described in example 3Bc–d; mp 207°–209° C.; $^1$H-NMR (DMSO-d$_6$): δ 0.87 (distorted t, 3H), 1.28 (m, 6H), 1.51 (m, 2H), 3.17 (q, 2H), 7.05 (s, 1H), 7.30 (br. s, 1H), 11.01 (s, 1H).

Example 8

6-Chloro-3-tetradecylamino-4H-thieno[3,2-e]-1,2,4-thiadiazine 1,1-dioxide

The title compound was prepared from 3-amino-5-chlorothiophene-2-sulfonamide hydrochloride and n-tetradecyl isothiocyanate by a procedure analogous to the procedure described in example 3Bc–d; mp 157°–158° C.; $^1$H-NMR (DMSO-d$_6$): δ 0.85 (distorted t, 3H), 1.25 (m, 22H), 1.50 (m, 2H), 3.19 (q, 2H), 7.05 (s, 1H), 7.26 (br. s, 1H), 10.95 (br. s, 1H).

Example 9

6-Chloro-3-methylamino-4H-thieno[3,2-e]-1,2,4-thiadiazine 1,1-dioxide

The title compound was prepared from 3-amino-5-chlorothiophene-2-sulfonamide hydrochloride and methyl isothiocyanate by a procedure analogous to the procedure described in example 3Bc–d; mp >190° C. decomp.; $^1$H-NMR (DMSO-d$_6$): δ 2.75 (s, 3H), 7.02 (s, 1H), 7.25 (br, 1H), 11.3 (br s, 1H).

Example 10

3-Benzylamino-6-chloro-4H-thieno[3,2-e]-1,2,4-thiadiazine 1,1-dioxide

The title compound was prepared from 3-amino-5-chlorothiophene-2-sulfonamide hydrochloride and benzyl isothiocyanate by a procedure analogous to the procedure described in example 3Bc–d; mp 223°–226° C.; $^1$H-NMR (DMSO-d$_6$): δ 4.42 (d, 2H), 7.05 (s, 1H), 7.30 (m, 5H), 7.78 (br t, 1H), 11.22 (br s, 1H).

Example 11

6-Chloro-3-octylamino-4H-thieno[3,2-e]-1,2,4-thiadiazine 1,1-dioxide

The title compound was prepared from 3-amino-5-chlorothiophene-2-sulfonamide hydrochloride and n-octyl isothiocyanate by a procedure analogous to the procedure described in example 3Bc–d; mp >190° C. decomp.; $^1$H-NMR (DMSO-d$_6$): δ 0.85 (t, 3H), 1.28 (m, 10H), 1.50 (m, 2H), 3.18 (q, 2H), 7.03 (s, 1H), 7.25 (br. s, 1H), 10.2 (br. s, 1H).

Example 12

6-Chloro-3-isobutylamino-4H-thieno[3,2-e]-1,2,4-thiadiazine 1,1-dioxide

The title compound was prepared from 3-amino-5-chlorothiophene-2-sulfonamide hydrochloride and isobutyl isothiocyanate by a procedure analogous to the procedure described in example 3Bc–d; mp 262°–264° C.; $^1$H-NMR (DMSO-d$_6$): δ 0.90 (d, 6H), 2.85 (m, 1H), 3.02 (t, 2H), 7.08 (s, 1H), 7.3 (br. s, 1H), 10.9 (br. s, 1H).

Example 13

6-Chloro-3-(4-phenylbutyl)amino-4H-thieno[3,2-e]-1,2,4-thiadiazine 1,1-dioxide

The title compound was prepared from 3-amino-5-chlorothiophene-2-sulfonamide hydrochloride and 4-phenylbutyl isothiocyanate by a procedure analogous to the procedure described in example 3Bc–d; mp 201°–205° C.; $^1$H-NMR (DMSO-d$_6$): δ 1.55 (m, 4H), 2.6 (t, 2H), 3.2 (q, 2H), 7.04 (s, 1H), 7.1–7.4 (m, 6H), 10.94 (br. s, 1H).

Example 14

6-Chloro-3-(1,5-dimethylhexyl)amino-4H-thieno[3,2-e]-1,2,4-thiadiazine 1,1-dioxide The title compound was prepared from 3-amino-5-chlorothiophene-2-sulfonamide hydrochloride and 1,5-dimethylhexyl isothiocyanate by a procedure analogous to the procedure described in example 3Bc–d; mp 197°–199° C. (ethyl acetate); $^1$H-NMR (DMSO-d$_6$): δ 0.85 (d, 6H), 1.12 (d, 3H), 1.1–1.6 (m, 7H), 3.77 (m, 1H), 7.07 (s, 1H), 7.12 (br. s, 1H), 10.72 (br. s, 1H).

Example 15

6-Chloro-3-propylamino-4H-thieno[3,2-e]-1,2,4-thiadiazine 1,1-dioxide

The title compound was prepared from 3,6-dichloro-4H-thieno[3,2-e]-1,2,4-thiadiazine 1,1-dioxide and n-propylamine by a procedure analogous to the procedure described in example 1Bb, except that the mixture was stirred for 16 h at 60° C.; mp 258°–261° C. (ethyl acetate); $^1$H-NMR (DMSO-d$_6$): δ 0.89 (t, 3H), 1.52 (sext, 2H), 3.15 (q, 2H), 7.05 (s, 1H), 7.29 (br. s, 1H), 10.95 (br. s, 1H).

Example 16

(R)-6-Chloro-3-(2-hydroxy-1-methylethyl)amino-4H-thieno[3,2-e]-1,2,4-thiadiazine 1,1-dioxide The title compound was prepared from 3,6-dichloro-4H-thieno[3,2-e]-1,2,4-thiadiazine 1,1-dioxide and (R)-(−)-2-amino-1-propanol by a procedure analogous to the procedure described in example 1Bb; mp 203°–204° C. (water), $^1$H-NMR (DMSO-d$_6$): δ 1.11 (d, 3H), 3.4 (d, 2H), 3.78 (m, 1H), 4.95 (br. s, 1H), 7.05 (br. s, 1H), 7.09 (s, 1H), 10.8 (br. s, 1H).

Example 17

(S)-6-Chloro-3-(2-hydroxy-1-methylethyl)amino4H-thieno[3,2-e]-1,2,4-thiadiazine 1,1-dioxide The title compound was prepared from 3,6dichloro-4H-thieno[3,2-e]-1,2,4-thiadiazine 1,1-dioxide and L-alaninol by a procedure analogous to the procedure described in example 1Bb; mp 204°–206° C. (water), $^1$H-NMR (DMSO-d$_6$): δ 1.11 (d, 3H), 3.4 (d, 2H), 3.78 (m, 1H), 4.95 (br. s, 1H), 7.05 (br. s, 1H), 7.09 (s, 1H), 10.8 (br. s, 1H).

Example 18

(R)-3-sec-Butylamino-6-chloro-4H-thieno[3,2-e]-1,2,4-thiadiazine 1,1-dioxide

The title compound was prepared from 3,6-dichloro-4H-thieno[3,2-e]-1,2,4-thiadiazine 1,1-dioxide and (R)-(−)-sec-butylamine by a procedure analogous to the procedure described in example 1Bb; mp 215°–220° C. (water), $^1$H-NMR (DMSO-d$_6$): δ 0.88 (t. 3H), 1.11 (d, 3H), 1.48 (m, 2H), 3.69 (m, 1H), 7.07 (s, 1H), 7.14 (br. s, 1H), 10.75 (br. s, 1H).

Example 19

3-Butylamino-6-chloro-4H-thieno[3,2-e]-1,2,4-thiadiazine 1,1-dioxide

The title compound was prepared from 3-amino-5-chlorothiophene-2-sulfonamide hydrochloride and n-butylamino isothiocyanate by a procedure analogous to the procedure described in example 3Bc–d; mp 218°–219° C.; $^1$H-NMR (DMSO-d$_6$): δ 0.90 (t, 3H), 1.35 (sext, 2H), 1.50 (quint, 2H), 3.18 (q, 2H), 7.02 (s, 1H), 7.25 (br. s, 1H), 10.95 (br. s, 1H).

Example 20

3-Isopropylamino-7-methyl-4,7-dihydro-pyrazolo[4,3-e][1,2,4]thiadiazine 1,1-dioxide a) 1-Methyl-5-sulfamoylpyrazole-4-carbohydrazide Ethyl 1-methyl-5sulfamoylpyrazole-4-carboxylate (1.0 g), prepared according to Bellemin and Festal, J. Heterocycl. Chem. 1984, 21, 1017, was stirred with 1 ml of hydrazine monohydrate at room temperature for 3 h and then evaporated to dryness. The residue was taken up in 5 ml of water and extracted with 25 ml of dichloromethane. The aqueous phase was evaporated to give 0.85 g (90%) of the title compound as a slowly crystallizing oil. Trituration with 5 ml of a 2:1 mixture of methanol and ethyl acetate gave a pure product: m.p. 172°–173° C.

b) 1-Methyl-4-(azidocarbonyl)pyrazole-5-sulfonamide

A solution of sodium nitrite (0.19 g) in 5 ml of water was added dropwise to a stirred solution of 1-methyl-5-sulfamoylpyrazole-4-carbohydrazide (0.55 g) in 8 ml of 1M hydrochloric acid at 0° C. The resulting mixture was stirred for 15 min and then filtered. The filter cake was washed with water and dried in vacuum to give 0.29 g (47%) of the title compound as a crystalline solid. The product was pure according to TLC (ethyl acetate) and was used immediately for the next step.

c) 1-Methyl-4-(ethoxycarbonylamino)pyrazole-5-sulfonamide

1-Methyl-4-(azidocarbonyl)pyrazole-5-sulfonamide (0.29 g) was added over 5 min. to 10 ml of abs. ethanol at reflux temperature. The resulting solution was refluxed for 15 min. and then evaporated to give 0.33 g of the title compound as a yellow oil containing a small residue of ethanol. The product was used without purification for the next step.

d) N-(4-Ethoxycarbonylamino-1-methyl-5-pyrazolesulfonyl)-N'-isopropylthiourea

A mixture of 1-methyl-4-(ethoxycarbonylamino) pyrazole-5-sulfonamide (0.42 g), potassium carbonate (0.34 g) and isopropyl isothiocyanate (280 μl) in 10 ml of dry acetone was heated at 55° C. for 18 h and then evaporated to dryness. The residue was dissolved in 10 ml of water, and pH was adjusted to 2 by dropwise addition of 4M hydrochloric acid. The precipitate was filtered off, rinsed with a small amount of water and dried to give 0.38 g (64%) of the title compound; m.p. 141°–144° C.

e) 4-Ethoxycarbonyl-3-isopropylamino-7-methyl-4,7-dihydropyrazolo[4,3-e][1,2,4]thiadiazine 1,1-dioxide To a stirred solution of N-(4-ethoxycarbonylamino-1-methyl-5-pyrazolesulfonyl)-N'-isopropylthiourea (0.37 g) and triethylamine (0.45 ml) in 5 ml of dry THF at 0° C. was added 1.0 ml of a 20% solution of phosgene in toluene. The mixture was stirred at 0° C. for 30 min. and then evaporated to dryness. The residue was triturated with 10 ml of water, filtered off, rinsed on the filter with water and dried to give 0.27 g (82%) of the title compound; m.p. 141°–145° C.

f) 3-Isopropylamino-7-methyl-4,7-dihydro-pyrazolo[4,3-e][1,2,4]thiadiazine 1,1-dioxide A mixture of 4-ethoxycarbonyl-5-isopropylamino-1-methyl-1,4-dihydro-pyrazolo[4,3-e][1,2,4]thiadiazine 7,7-dioxide (0.23 g) and 2 ml of 2M aqueous sodium hydroxide was heated at reflux for 2 h. Then the mixture was cooled to room temperature and pH was adjusted to 2 by dropwise addition of 4M hydrochloric acid. After stirring for 15 min. the precipitate was filtered off, rinsed with a small amount of water and dried to give 0.11 g (61%) of the title compound; m.p. 242°–243° C.; $^1$H-NMR (DMSO-d$_6$): δ (ppm) 10.25 (s, 1H, NH), 7.42 (s, 1H, 3-H), 7.21 (br d, 1H, NH), 3.98–3.75 (m, 4H, CH and N-CH$_3$), 1,15 (d, 6H, CH$_3$).

Example 21

3-Isopropyl-6-methyl-4H-thiazolo[4,5-e]-1,2,4-thiadiazine 1,1-dioxide

The title compound may be prepared by a similar procedure as described in example 20 starting with ethyl 2-methyl-5-sulfamoylthiazole-4-carboxylate, which in turn was prepared according to Tamura et al. Chem. Pharm. Bull. 1971, 19, 119.

What is claimed is:
1. A compound of formula I

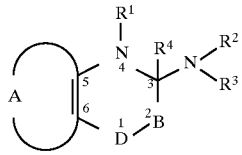

wherein B is NR$^5$ or CR$^5$R$^6$, wherein R$^5$ and R$^6$ independently are (1) hydrogen, (2) hydroxy, (3) C$_{1-6}$-alkoxy, (4) C$_{1-6}$-alkyl, (5) C$_{3-6}$-cycloalkyl, (6) C$_{2-6}$-alkenyl or (7) C$_{2-6}$-alkynyl, wherein (4) to (7) are optionally mono- or polysubstituted with halogen, or R$^5$ and R$^4$ together form a bond;

D is —S(=O)$_2$— or —S(=O)—; or

D—B is —S(=O)(R$^7$)=N— wherein R$^7$ is (1) C$_{1-6}$-alkyl, (2) aryl or (3) heteroaryl, wherein (2) and (3) are optionally mono- or polysubstituted with halogen, hydroxy, C$_{1-6}$-alkoxy, aryloxy, arylalkoxy, nitro, amino, C$_{1-6}$-monoalkyl- or dialkylamino, cyano, acyl, or C$_{1-6}$-alkoxycarbonyl;

R$^1$ is (1) hydrogen, (2) hydroxy, (3) C$_{1-6}$-alkoxy, (4) C$_{1-6}$-alkyl, (5) C$_{3-6}$-cycloalkyl, (6) C$_{2-6}$-alkenyl or (7) C$_{2-6}$-alkynyl, wherein (4) to (7) are optionally mono- or polysubstituted with halogen and R$^4$ is hydrogen, or R$^4$ together with R$^5$ form a bond, or R$^1$ together with R$^4$ form a bond;

R$^2$ is (1) hydrogen, (2) hydroxy, (3) C$_{1-6}$-alkoxy, (4) C$_{1-6}$-alkyl, (5) C$_{3-6}$-cycloalkyl, (6) C$_{2-6}$-alkenyl or (7) C$_{2-6}$-alkynyl, wherein (4) to (7) are optionally mono- or polysubstituted with halogen;

R$^3$ is (1) R$^8$, (2) —OR$^8$, (3) —C(=X)R$^8$, (4) —NR$^8$R$^9$, (5) bicycloalkyl, (6) aryl, (7) heteroaryl, (8) arylalkyl or (9) heteroarylalkyl, wherein (5) to (9) are optionally mono- or polysubstituted with halogen, hydroxy, C$_{1-6}$-alkoxy, aryloxy, arylalkoxy, nitro, amino, C$_{1-6}$-monoalkyl- or dialkylamino, cyano, oxo, acyl or C$_{1-6}$-alkoxycarbonyl, or (10) aryl substituted with C$_{1-6}$-alkyl;

wherein R$^8$ is (1) hydrogen, (2) C$_{3-6}$-cycloalkyl, (3) (C$_{3-6}$-cycloalkyl)C$_{1-6}$-alkyl, wherein the C$_{3-6}$-cycloalkyl group in (2) and (3) is optionally being mono- or polysubstituted with C$_{1-6}$-alkyl, halogen, hydroxy or C$_{1-6}$-alkoxy, (4) a 3–6 membered saturated ring system comprising at least one nitrogen-, oxygen- or sulfur atom, or (5) straight or branched C$_{1-18}$-alkyl optionally mono- or polysubstituted with halogen, hydroxy, C$_{1-6}$-alkoxy, C$_{1-6}$-alkylthio, C$_{3-6}$-cycloalkyl, aryl, aryloxy, arylalkoxy, nitro, amino, C$_{1-6}$-monoalkyl- or dialkylamino, cyano, oxo, formyl, acyl, carboxy, C$_{1-6}$-alkoxycarbonyl, or carbamoyl;

X is O or S;

R$^9$ is (1) hydrogen, (2) C$_{1-6}$-alkyl, (3) C$_{2-6}$-alkenyl, or (4) C$_{3-6}$-cycloalkyl optionally mono- or polysubstituted with C$_{1-6}$-alkyl, halogen, hydroxy or C$_{1-6}$-alkoxy, or R$^8$ and R$^9$ together with the nitrogen atom form a 3–12 membered mono- or bicyclic system, in which at least one of the carbon atoms may be replaced with nitrogen, oxygen or sulfur, each of these ring systems optionally being mono- or polysubstituted with halogen, C$_{1-6}$-alkyl, hydroxy, C$_{1-6}$-alkoxy, C$_{1-6}$-alkoxy-C$_{1-6}$-alkyl, nitro, amino, cyano, trifluoromethyl, C$_{1-6}$-monoalkyl- or dialkylamino, oxo, or R$^3$ is

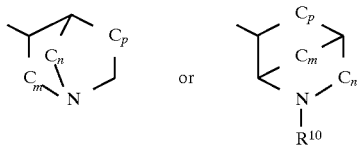

wherein n, m, p independently are 0, 1, 2, or 3 and R$^{10}$ is (1) hydrogen, (2) hydroxy, (3) C$_{1-6}$-alkoxy, (4) C$_{3-6}$-cycloalkyl optionally mono- or polysubstituted with C$_{1-6}$-alkyl, halogen, hydroxy or C$_{1-6}$-alkoxy, (5) C$_{1-6}$-alkyl, (6) C$_{2-6}$-alkenyl or (7) C$_{2-6}$-alkynyl, wherein (5) to (7) are optionally mono- or polysubstituted with halogen, or R$^2$ and R$^3$ together with the nitrogen atom forms a 3–12 membered mono- or bicyclic system, in which at least one of the carbon atoms may be replaced with nitrogen, oxygen or sulfur, each of these ring systems optionally being mono- or polysubstituted with halogen, C$_{1-6}$-alkyl, hydroxy, C$_{1-6}$-alkoxy, C$_{1-6}$-alkoxy-C$_{1-6}$-alkyl, nitro, amino, cyano, trifluoromethyl, C$_{1-6}$-monoalkyl- or dialkylamino or oxo; and A together with carbon atoms 5 and 6 of formula I form a 5 or 6 membered heterocyclic system comprising at least one nitrogen-, oxygen- or sulfur atom, the heterocyclic system optionally being mono- or polysubstituted with (1) halogen, (2) C$_{1-12}$-alkyl, (3) C$_{3-6}$-cycloalkyl, (4) hydroxy, (5) C$_{1-6}$-alkoxy, (6) C$_{1-6}$-alkoxy-C$_{1-6}$-alkyl, (7) nitro, (8) amino, (9) cyano, (10) cyanomethyl, (11) perhalomethyl, (12) C$_{1-6}$-monoalkyl- or dialkylamino, (13) sulfamoyl, (14) C$_{1-6}$-alkylthio, (15) C$_{1-6}$-alkylsulfonyl, (16) C$_{1-6}$-alkylsulfinyl, (17) C$_{1-6}$-alkylcarbonylamino, (18) arylthio, (19) arylsulfinyl, (20) arylsulfonyl, wherein the aryl group in (18) to (20) is optionally mono- or polysubstituted with C$_{1-6}$-alkyl, halogen, hydroxy or C$_{1-6}$-alkoxy, (21) C$_{1-6}$-alkoxycarbonyl, (22) C$_{1-6}$-alkoxycarbonyl-C$_{1-6}$-alkyl, (23) carbamyl, (24) carbamylmethyl, (25) C$_{1-6}$-monoalkyl- or dialkylaminocarbonyl, (26) C$_{1-6}$-monoalkyl- or dialkylaminothiocarbonyl, (27) ureido, (28) C$_{1-6}$-monoalkyl- or dialkylaminocarbonylamino, (29) thioureido, (30) C$_{1-6}$-monoalkyl- or dialkylaminothiocarbonylamino, (31) C$_{1-6}$-monoalkyl- or dialkylaminosulfonyl, (32) carboxy, (33) carboxy-C$_{1-6}$-alkyl, (34) acyl, (35) aryl, (36) arylalkyl, (37) aryloxy, wherein the aryl group in (35) to (37) is optionally mono- or polysubstituted with C$_{1-6}$-alkyl, halogen, hydroxy or C$_{1-6}$-alkoxy, (38) (1,2,4-oxadiazol-5-yl)-C$_{1-6}$-alkyl, (39) (1,2,4-oxadiazol-3-yl)-C$_{1-6}$-alkyl, wherein the oxadiazolyl group in (38) and (39) is optionally substituted with C$_{1-6}$-alkyl or C$_{3-6}$-cycloalkyl, or (40) a 5–6 membered nitrogen containing ring, optionally substituted with phenyl or C$_{1-6}$-alkyl;

provided that A together with carbon atoms 5 and 6 of formula I do not form a pyridine ring and that the following compounds 3-aminoimidazo[4,5-e]-1,2,4-thiadiazine 1,1-dioxide and 3-(benzoylamino)imidazo [4,5-e]-1,2,4-thiadiazine 1,1-dioxide are not included; or a pharmaceutically acceptable salt thereof with a pharmaceutically acceptable acid or base;

an optical isomer thereof; or a tautomeric form thereof.

2. A compound of claim 1, wherein $R^2$ is hydrogen or $C_{1-6}$-alkyl.

3. A compound of claim 1, wherein $R^3$ is (1) $R^8$, (2) —$OR^8$, (3) $NR^8R^9$ or (4) aryl, the aryl groups optionally being substituted with $C_{1-6}$-alkyl, wherein $R^8$ is (1) hydrogen, (2) $C_{3-6}$-cycloalkyl, (3) ($C_{3-6}$-cycloalkyl)$C_{1-6}$-alkyl, (4) a 3–6 membered saturated ring system comprising one, two or three nitrogen-, oxygen- or sulfur atoms, or (5) straight or branched $C_{1-18}$-alkyl optionally substituted with halogen, hydroxy, $C_{1-6}$-alkoxy, $C_{1-6}$-alkylthio, $C_{3-6}$-cycloalkyl or aryl, $R^9$ is hydrogen, $C_{1-6}$-alkyl or $C_{3-6}$-cycloalkyl, or $R^8$ and $R^9$ together with the nitrogen atom form a 4–6 membered ring.

4. A compound of claim 1, wherein $R^3$ is secondary $C_{3-6}$-alkyl, tertiary $C_{4-6}$-alkyl, $C_{3-6}$-cycloalkyl or ($C_{3-6}$-cycloalkyl)methyl.

5. A compound of claim 1, wherein A together with carbon atoms 5 and 6 of formula I form a 5 membered heterocyclic system containing one hetero atom selected from nitrogen and sulfur, the heterocyclic system optionally being mono- or disubstituted with (1) halogen, (2) $C_{1-12}$-alkyl, (3) $C_{3-6}$-cycloalkyl, (4) cyano, (5) cyanomethyl, (6) perhalomethyl, (7) sulfamoyl, (8) $C_{1-6}$-alkylthio, (9) $C_{1-6}$-alkylsulfonyl, (10) $C_{1-6}$-alkylsulfinyl, (11) arylthio, (12) arylsulfinyl, (13) arylsulfonyl, the aryl group in (11) to (13) is optionally mono- or polysubstituted with $C_{1-6}$-alkyl, halogen, hydroxy or $C_{1-6}$-alkoxy, (14) $C_{1-6}$-alkoxycarbonyl-$C_{1-6}$-alkyl, (15) carbamylmethyl, (16) carboxy-$C_{1-6}$-alkyl, (17) aryloxy, (18) (1,2,4-oxadiazol-5-yl) $C_{1-6}$-alkyl or (19) (1,2,4-oxadiazol-3-yl)$C_{1-6}$-alkyl, wherein the oxadiazolyl group in (18) and (19) is optionally substituted with $C_{1-6}$-alkyl or $C_{3-6}$-cycloalkyl, (20) acyl or (21) a 5–6 membered nitrogen containing ring, optionally substituted with phenyl or $C_{1-6}$-alkyl.

6. A compound of claim 1, wherein A together with carbon atoms 5 and 6 of formula I form a 5 membered heterocyclic system containing two hetero atoms selected from nitrogen, oxygen and sulfur, the heterocyclic system optionally being substituted with (1) halogen, (2) $C_{1-12}$-alkyl, (3) $C_{3-6}$-cycloalkyl, (4) cyano, (5) cyanomethyl, (6) perhalomethyl, (7) sulfamoyl, (8) $C_{1-6}$-alkylsulfonyl, (9) $C_{1-6}$-alkylsulfinyl, (10) arylthio, (11) arylsulfinyl, (12) arylsulfonyl, wherein the aryl group in (10) to (12) is optionally mono- or polysubstituted with $C_{1-6}$-alkyl, halogen, hydroxy or $C_{1-6}$-alkoxy, (13) $C_{1-6}$-alkoxycarbonyl-$C_{1-6}$-alkyl, (14) carbamylmethyl, (15) carboxy-$C_{1-6}$-alkyl, (16) aryloxy, (17) (1,2,4-oxadiazol-5-yl) $C_{1-6}$-alkyl, or (18) (1,2,4-oxadiazol-3-yl)$C_{1-6}$-alkyl, wherein the oxadiazolyl group in (17) and (18) is optionally substituted with $C_{1-6}$-alkyl or $C_{3-6}$-cycloalkyl, (19) acyl, or (20) a 5–6 membered nitrogen containing ring, optionally substituted with phenyl or $C_{1-6}$-alkyl.

7. A compound of claim 1, wherein A together with carbon atoms 5 and 6 of formula I forms a 6 membered aromatic heterocyclic system containing two or three nitrogen atoms, the heterocyclic system optionally being substituted with (1) halogen, (2) $C_{1-12}$-alkyl, (3) $C_{3-6}$-cycloalkyl, (4) cyano, (5) cyanomethyl, (6) perhalomethyl, (7) sulfamoyl, (8) $C_{1-6}$-alkylsulfonyl, (9) $C_{1-6}$-alkylsulfinyl, (10) arylthio, (11) arylsulfinyl, (12) arylsulfonyl, wherein the aryl group in (10) to (12) is optionally mono- or polysubstituted with $C_{1-6}$-alkyl, halogen, hydroxy or $C_{1-6}$-alkoxy, (13) $C_{1-6}$-alkoxycarbonyl-$C_{1-6}$-alkyl, (14) carbamylmethyl, (15) carboxy-$C_{1-6}$-alkyl, (16) aryloxy, (17) (1,2,4-oxadiazol-5-yl)$C_{1-6}$-alkyl, or (18) (1,2,4-oxadiazol-3-yl)$C_{1-6}$-alkyl, wherein the oxadiazolyl group in (17) and (18) is optionally substituted with $C_{1-6}$-alkyl or $C_{3-6}$-cycloalkyl, (19) acyl, or (20) a 5–6 membered nitrogen containing ring, optionally substituted with phenyl or $C_{1-6}$-alkyl.

8. A compound of claim 1, wherein A together with carbon atoms 5 and 6 of formula I forms a 6 membered non-aromatic heterocyclic system containing one or two hetero atoms selected from nitrogen, oxygen and sulfur, the heterocyclic system optionally being substituted with (1) halogen, (2) $C_{1-12}$-alkyl, (3) $C_{3-6}$-cycloalkyl, (4) cyano, (5) cyanomethyl, (6) perhalomethyl, (7) sulfamoyl, (8) $C_{1-6}$-alkylthio, (9) $C_{1-6}$-alkylsulfonyl, (10) $C_{1-6}$-alkylsulfinyl, (11) arylthio, (12) arylsulfinyl, (13) arylsulfonyl, the aryl group in (11) to (13) is optionally mono- or polysubstituted with $C_{1-6}$-alkyl, halogen, hydroxy or $C_{1-6}$-alkoxy, (14) $C_{1-6}$-alkoxycarbonyl-$C_{1-6}$-alkyl, (15) carbamylmethyl, (16) carboxy-$C_{1-6}$-alkyl, (17) aryloxy, (18) (1,2,4-oxadiazol-5-yl)$C_{1-6}$-alkyl or (19) (1,2,4-oxadiazol-3-yl)$C_{1-6}$-alkyl, wherein the oxadiazolyl group in (18) and (19) is optionally substituted with $C_{1-6}$-alkyl or $C_{3-6}$-cycloalkyl, (20) acyl or (21) a 5–6 membered nitrogen containing ring, optionally substituted with phenyl or $C_{1-6}$-alkyl.

9. A compound of claim 1, wherein the formula I is

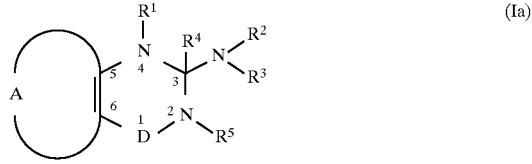

wherein $R^1$ and $R^5$ independently are (1) hydrogen, (2) hydroxy, (3) $C_{1-6}$-alkoxy, or (4) $C_{1-6}$-alkyl, (5) $C_{3-6}$-cycloalkyl, (6) $C_{2-6}$-alkenyl or (7) $C_{2-6}$-alkynyl, wherein (4) to (7) are optionally mono- or polysubstituted with halogen and $R^4$ is hydrogen, or $R^4$ together with $R^5$ form a bond, or $R^4$ together with $R^1$ form a bond; and D is —S(=O)$_2$— or S(=O)—.

10. A compound of claim 9, wherein $R^1$ and $R^5$ independently are hydrogen or $C_{1-6}$-alkyl.

11. A compound of claim 9, wherein $R^1$ together with $R^4$ form a bond.

12. A compound of claim 9, wherein $R^4$ together with $R^5$ form a bond.

13. A compound of claim 9, wherein D is —S(=O)$_2$—.

14. A compound of claim 1, wherein formula I is

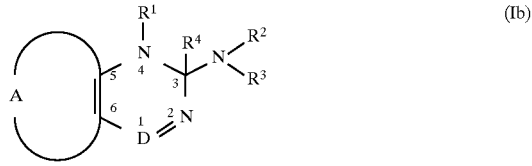

wherein $R^1$ is (1) hydrogen, (2) hydroxy, (3) $C_{1-6}$-alkoxy, (4) $C_{1-6}$-alkyl, (5) $C_{3-6}$-cycloaklyl, (6) $C_{2-6}$-alkenyl or (7) $C_{2-6}$-alkynyl, wherein (4) to (7) are optionally mono- or polysubstituted with halogen and $R^4$ is hydrogen, or $R^4$ together with $R^1$ form a bond;

D is —S(=)$R^7$= wherein $R^7$ is (1) $C_{1-6}$-alkyl, (2) aryl or (3) heteroaryl, wherein (2) and (3) are optionally mono- or polysubstituted with halogen, hydroxy, $C_{1-6}$-alkoxy, aryloxy, arylalkoxy, nitro, amino, $C_{1-6}$-monoalkyl- or dialkylamino, cyano, acyl or $C_{1-6}$-alkoxycarbonyl.

15. A compound of claim 14, wherein $R^1$ is hydrogen or $C_{1-6}$-alkyl.

16. A compound of claim 14, wherein $R^1$ together with $R^4$ form a bond.

17. A compound of claim 14, wherein $R^7$ is $C_{1-6}$-alkyl, phenyl or pyridyl.

18. A compound of claim 1, wherein formula I is

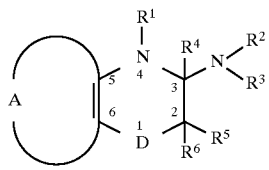
(Ic)

wherein $R^1$, $R^5$ and $R^6$ independently are (1) hydrogen, (2) hydroxy, (3) $C_{1-6}$-alkoxy, (4) $C_{1-6}$-alkyl, (5) $C_{3-6}$-cycloalkyl, (6) $C_{2-6}$-alkenyl or (7) $C_{2-6}$-alkynyl, wherein (4) to (7) are optionally mono- or polysubstituted with halogen and $R^4$ is hydrogen, or $R^4$ together with $R^5$ form a bond, or $R^4$ together with $R^1$ form a bond; and D represents —S(=O)$_2$— or —S(=O)—.

19. A compound of claim 18, wherein $R^1$, $R^5$ and $R^6$ independently are hydrogen or $C_{1-6}$-alkyl.

20. A compound of claim 18, wherein $R^1$ together with $R^4$ form a bond.

21. A compound of claim 18, wherein $R^4$ together with $R^5$ form a bond.

22. A compound of claim 18, wherein D is —S(=O)$_2$—.

23. A compound selected from the following:
6-Chloro-3-(1,2-dimethylpropyl)amino-4H-thieno[3,2-e]-1,2,4-thiadiazine 1,1-dioxide;
6-Chloro-3-ethylamino-4H-thieno[3,2-e]-1,2,4-thiadiazine 1,1-dioxide;
6-Chloro-3-isopropylamino-4H-thieno[3,2-e]-1,2,4thiadiazine 1,1-dioxide;
(S)-6-Chloro-3-(1-phenylethyl)amino-4H-thieno[3,2-e]-1,2,4thiadiazine 1,1 -dioxide;
3-Allylamino-6chloro-4H-thieno[3,2-e]-1,2,4thiadiazine 1,1-dioxide;
6-Chloro-3-cyclopropylamino-4H-thieno[3,2-e]-1,2,4-thiadiazine 1,1-dioxide;
6-Chloro-3-hexylamino-4H-thieno[3,2-e]-1,2,4-thiadiazine 1,1-dioxide;
6-Chloro-3-tetradecylamino-4H-thieno[3,2-e]-1,2,4-thiadiazine 1,1-dioxide;
6-Chloro-3-methylamino-4H-thieno[3,2-e]-1,2,4-thiadiazine 1,1-dioxide;
3-Benzylamino-6-chloro-4H-thieno[3,2-e]-1,2,4-thiadiazine 1,1dioxide;
6-Chloro-3-octylamino-4H-thieno[3,2-e]-1,2,4-thiadiazine 1,1-dioxide;
6-Chloro-3-isobutylamino-4H-thieno[3,2-e]-1,2,4-thiadiazine 1,1-dioxide;
6-Chloro-3-(4-phenylbutyl)amino-4H-thieno[3,2-e]-1,2,4-thiadiazine 1,1-dioxide;
6-Chloro-3-(1,5-dimethylhexyl)amino-4H-thieno[3,2-e]-1,2,4-thiadiazine 1,1-dioxide;
6-Chloro-3-propylamino-4H-thieno[3,2-e]-1,2,4-thiadiazine 1,1-dioxide;
(R)-6-Chloro-3-(2-hydroxy-1-methylethyl)amino-4H-thieno[3,2e]-1,2,4-thiadiazine 1,1-dioxide;
(S)-6-Chloro-3-(2-hydroxy-1-methylethyl)amino-4H-thieno[3,2-e]-1,2,4-thiadiazine 1,1-dioxide;
(R)-3-sec-Butylamino-6-chloro-4H-thieno[3,2-e]-1,2,4thiadiazine 1,1-dioxide;
3-Butylamino-6-chloro-4H-thieno[3,2e]-1,2,4-thiadiazine 1,1dioxide; and
3-Isopropylamino-7-methyl-4,7-dihydro-pyrazolo[4,3-e][1,2,4]thiadiazine 1,1-dioxide.

24. A method of preparing a compound of formula I, comprising:
a) reacting a compound of formula II

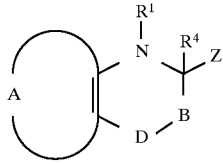
(II)

wherein Z is a leaving group selected from alkoxy, alkylthio, halogen, trimethylamino, and methylsulfonyl, with a compound of formula III:

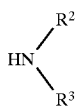
(III)

to form a compound of formula I;
b) reacting a compound of formula IV

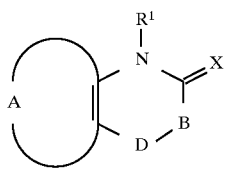
(IV)

wherein $R^1$ is hydrogen or B is NH, with the compound of formula III, or a suitable salt thereof in the presence of $P_2O_5$ and a high boiling tertiary amine or a suitable salt thereof, to form a compound of formula I;
c) reacting a compound of the formula IV

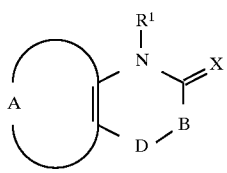
(IV)

wherein $R^1$ is hydrogen or B is NH, with a compound of the formula III, or a suitable salt thereof in the presence of titanium tetrachloride and a solvent with which it may form a complex to form a compound of formula I;
d) reacting a compound of formula V

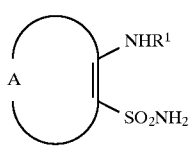
(V)

with a compound of formula VI $R^3$NCO     (VI)

to form a compound of formula I wherein D is $SO_2$, B is $NR^5$, $R^2$ is H, and $R^4$ and $R^5$ together form a bond;

e) reacting a compound of formula V

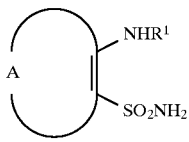
(V)

with a compound of formula VII

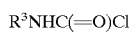
(VII)

to form a compound of formula I wherein D is $SO_2$, B is $NR^5$, $R^2$ is H, and $R^4$ and $R^5$ together form a bond;

f) reacting a compound of formula V

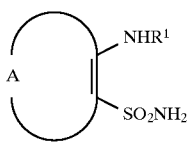
(V)

with a compound of formula VIII

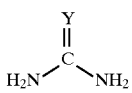
(VIII)

wherein Y is NH or S, or a suitable salt thereof, to form a compound of formula I, wherein D is $SO_2$, B is $NR^5$, $R^4$ and $R^5$ form a bond, and $R^2$ and $R^3$ are H;

g) reacting in the presence of a base a compound of formula IX

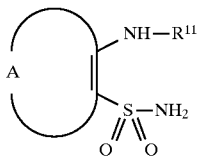
(IX)

or a suitable salt thereof, wherein $R^{11}$ is $R^1$ or EtOC(=O), with a compound of formula X

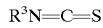
(X)

to form an adduct which may have either of the two structures XI or XII or be a mixture of the two

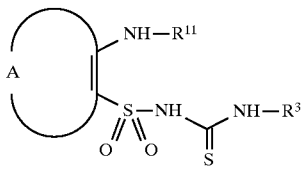
(XI)

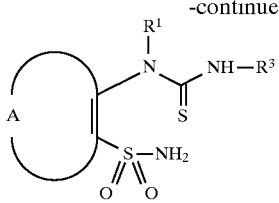
(XII)

either of which by ring-closure forms a compound of formula I, if $R^{11}$ is $R^1$, wherein D is $S(=O)_2$, B is $NR^5$, $R^2$ is H, and $R^4$ and $R^5$ together form a bond, and a compound of the formula XIII if $R^{11}$ is EtOC(=O);

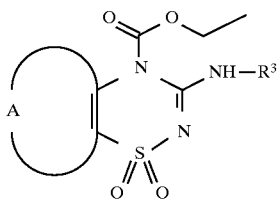
(XIII)

h) hydrolyzing and subsequently decarboxylating a compound of formula XIII

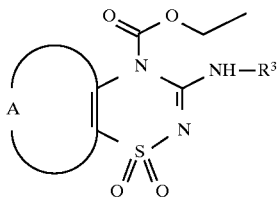
(XIII)

to form a compound of formula I, wherein D is $S(=O)_2$, B is $NR^5$, $R^1$ and $R^2$ are H, and $R^4$ and $R^5$ together form a bond.

25. A pharmaceutical composition comprising a compound of claim 1 together with a pharmaceutically acceptable carrier or diluent.

26. The pharmaceutical composition of claim 25 in the form of an oral dosage unit or parenteral dosage unit.

27. A method of treating diseases of the endocrinologic system, comprising administering to a subject in need thereof an effective amount of a compound of claim 1.

28. A method of treating diseases of the endocrinologic system, comprising administering to a subject in need thereof an effective amount of a composition of claim 25.

29. The method of claim 28, wherein the compound is administered as a dose ranging from about 0.05 mg to 1000 mg per day.

30. The method of claim 29, wherein the dose ranges from about 0.1 mg to 500 mg per day.

31. The method of claim 30, wherein the dose ranges from about 5 mg to 200 mg per day.

* * * * *